US008175348B2

(12) United States Patent
Van Uitert, Jr. et al.

(10) Patent No.: US 8,175,348 B2
(45) Date of Patent: May 8, 2012

(54) SEGMENTING COLON WALL VIA LEVEL SET TECHNIQUES

(75) Inventors: Robert L. Van Uitert, Jr., Germantown, MD (US); Ronald M. Summers, Potomac, MD (US); Ingmar Bitter, Ontario, CA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 1313 days.

(21) Appl. No.: 11/810,704

(22) Filed: Jun. 5, 2007

(65) Prior Publication Data

US 2008/0304616 A1 Dec. 11, 2008

(51) Int. Cl.
*G06K 9/00* (2006.01)

(52) U.S. Cl. ........................................................ 382/128

(58) Field of Classification Search ................... 382/128, 382/129–132
See application file for complete search history.

(56) References Cited

U.S. PATENT DOCUMENTS

| | | | |
|---|---|---|---|
| 5,274,718 A * | 12/1993 | Leonardi et al. | 382/240 |
| 5,971,767 A | 10/1999 | Kaufman et al. | |
| 6,046,179 A * | 4/2000 | Murch et al. | 514/62 |
| 6,246,784 B1 | 6/2001 | Summers et al. | |
| 6,331,116 B1 | 12/2001 | Kaufman et al. | |
| 6,343,936 B1 | 2/2002 | Kaufman et al. | |
| 6,345,112 B1 | 2/2002 | Summers et al. | |
| 6,556,696 B1 | 4/2003 | Summers et al. | |
| 6,775,401 B2 * | 8/2004 | Hwang et al. | 382/131 |
| 7,260,250 B2 | 8/2007 | Summers et al. | |
| 7,440,601 B1 | 10/2008 | Summers et al. | |
| 7,454,045 B2 | 11/2008 | Yao et al. | |
| 7,646,904 B2 | 1/2010 | Summers et al. | |
| 8,023,710 B2 | 9/2011 | Summers et al. | |
| 2004/0064029 A1 | 4/2004 | Summers et al. | |
| 2005/0078858 A1 | 4/2005 | Yao et al. | |
| 2005/0107695 A1 | 5/2005 | Kiraly et al. | |
| 2005/0152591 A1 | 7/2005 | Kiraly et al. | |
| 2006/0173272 A1 * | 8/2006 | Qing et al. | 600/407 |

(Continued)

FOREIGN PATENT DOCUMENTS

WO   WO 03058553   7/2003

OTHER PUBLICATIONS

11.D. J. Vining, Y. Ge, D. K. Ahn, and D. R. Stelts, K. Doi, H. MacMahon, M. L. Giger, and K. R. Hoffman, "Virtual colonoscopy with computer-assisted polyp detection", Jul. 1999, Computer-Aided Diagnosis in Medical Imaging, Elsevier Science B.V, pp. 445-452.*

(Continued)

*Primary Examiner* — Aaron W Carter
(74) *Attorney, Agent, or Firm* — Klarquist Sparkman, LLP

(57) ABSTRACT

Various level set techniques can be used to automatically segment the colon wall, including identifying the colon wall outer boundary. A speed image can be used during level set processing. For example, the speed image can be generated via inverting the gradient perpendicular to the segmented inner boundary of the colon wall. The techniques can be useful for determining wall thickness, which can be used to classify polyp candidates, diagnose diseases of the colon, and the like.

32 Claims, 37 Drawing Sheets
(17 of 37 Drawing Sheet(s) Filed in Color)

U.S. PATENT DOCUMENTS

| | | |
|---|---|---|
| 2008/0008367 A1 | 1/2008 | Franaszek et al. |
| 2008/0015419 A1 | 1/2008 | Summers et al. |
| 2008/0194946 A1 | 8/2008 | Summers et al. |
| 2009/0208409 A1 | 8/2009 | Summers et al. |
| 2010/0074491 A1 | 3/2010 | Summers et al. |

OTHER PUBLICATIONS

U.S. Appl. No. 10/961,681, filed Oct. 8, 2004, Summers et al.
U.S. Appl. No. 11/685,127, filed Mar. 12, 2007, Summers et al.
"Binary Space Partitioning," Wikipedia, visited Mar. 29, 2007, 4 pages. http://en.wikipedia.org/wiki/Binary_space_partitioning.
Franaszek et al, "Hybrid Segmentation of Colon Filled with Air and Opacified Fluid for CT Colonography," TMI, 2005, 13 pages.
"Level Set," Wikipedia, http://en.wikipedia.org/wiki/Level_set, visited Mar. 28, 2007, 2 pages.
"Level Set Methods: An initial value formulation," http://math.berkeley.edu/~sethian/2006/Explanations/level_set_explain.html, visited Mar. 28, 2007, 3 pages.
"Level Set Method" Wikipedia, http://en.wikipedia.org/wiki/Level_set_method, visited Mar. 28, 2007, 3 pages.
"Segmentation in Medical Imaging," http://math.berkeley.edu/~sethian/2006/Applications/Medical_Imaging/artery.html, visited Mar. 28, 2007, 2 pages.
Summers et al., "Colonic Polyps: Complementary Role of Computer-aided Detection in CT Colonography," *Radiology*, 2002, vol. 225, No. 2, pp. 391-399, 9 pages.
Summers et al., "Computed Tomographic Virtual Colonoscopy Computer-Aided Polyp Detection in a Screening Pppulation," *Gastroenterology*, 2005, vol. 129, pp. 1832-1844, 13 pages.
Van Uitert et al., "Automatic Correction of Level Set based Subvoxel Accurate Centerlines for Virtual Colonoscopy," *3rd IEEE International Symposium on Biomedical Imaging: Nano to Macro*, Apr. 6-9, 2006, 4 pages.
Van Uitert et al., "Colonic Wall Thickness using level sets for CT Virtual Colonoscopy Visual Assessment and Polyp Detection," *Medical Imaging 2007: Physiology, Function and Structure from Medical Images*, Mar. 29, 2007, 7 pages.
Van Uitert et al., "Computer-Aided Detection of Colonic Diverticular Disease," *4th IEEE International Symposium on Biomedical Imaging: Nano to Macro (IBSI 2007)*, Apr. 2007, 4 pages.
Van Uitert et al., "Detection of Colon Wall Outer Boundary and Segmentation of the Colon Wall Based on Level Set Methods," *Engineering in Medicine and Biology Society, EMBS '06, 28th Annual International Conference of the IEEE*, Aug. 2006, 4 pages.
Wang et al, "Reduction of false positives by internal features for polyp detection in CT-based virtual colonoscopy," *Medical Physics*, vol. 32, No. 12, Dec. 2005, pp. 3602-3616, 15 pages.
Zeng et al. "Segmentation and Measurement of the Cortex from 3-D MR Images Using Coupled Surfaces Propagation," *IEEE Transaction on Medical Imaging*, vol. 18, No. 10, Oct. 1999, pp. 100-111, 12 pages.
Zeng, Volumetric Layer Segmentation Using a Generic Shape Constraint with Applications to Cortical Shape Analysis, Abstract, Yale University 2000, 117 pages.
Van Uitert et al., "Automatic Correction of Level Set Based Subvoxel Precise Centerlines for Virtual Colonoscopy Using the Colon Outer Wall," *IEEE Transactions on Medical Imaging*, vol. 26, No. 8, Aug. 2007, pp. 1069-1078, 10 pages.
Gokturk, et al., "A New 3-D Volume Processing Method for Polyp Detection," Engineering in Medicine and Biology Society, 2001, Proceedings of the 23rd Annual International Conference of the IEEE, (2001) pp. 2522-2525.
Carrion et al., "could the Pollen Origin be Determined using Computer Vision," An Experimental Study, Visualization, Imaging, and Image Processing (2002) pp. 1-6.
Dehmeshki et al, "Multiresolution Active Contour Model Applied on Lung and Colon Images," Medical Imaging 2004; Proceedings of the SPIE, 5370 (2004), pp. 1685-1694.
Jerebko et al., "Computer-aided polyp detection in CT colonography using an ensemble of support vector machines," International Congress Series, 1256 (2003) pp. 1019-1024.
Ji et al., "Dynamic View Selection for Time-Varying Volumes," IEEE Transactions on Visualization and Computer Graphics, 12/5 (2006); pp. 1109-1116.
Karkanis et al., "Computer-Aided Tumor Detection in Endoscopic Video Using Color Wavelet Features," IEEE Transactions on Information Technology in Biomedicine, 7.2 (2003), pp. 141-152.
Lee et al., Automated Detection of pulmonary modules in Helical CT images based on a n improved template-matching technique, Jul. 2011, IEEE transactions on medical imaging, vol. 20, No. 7, 10 pages.
Lyu et al., "A Digital Technique for Art Authentication," PNAS, 101.49 (2004) pp. 17006-17010.
Vazquez et al., "Fast Adaptive Selection of Best Views," ICCSA 2003, LNCS 2669 (2003) pp. 295-305.
Vazquez et al., "Viewpoint Selection Using Viewpoint Entropy," Proceedings of Vision Modeling and Visualization Conference, (2001), pp. 273-280.

\* cited by examiner

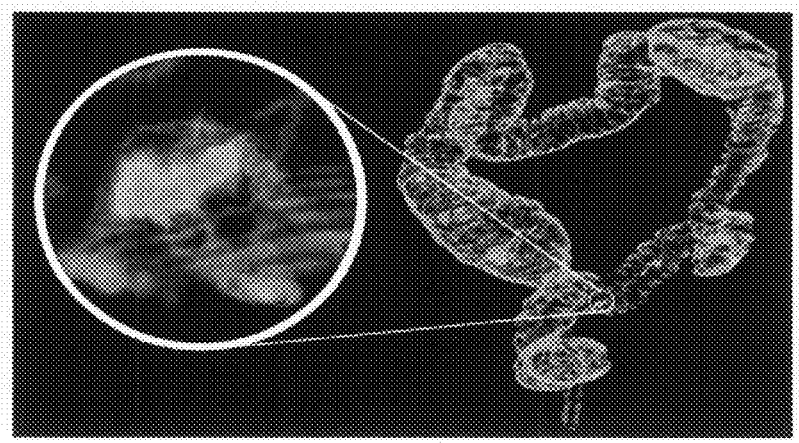
FIG. 27A
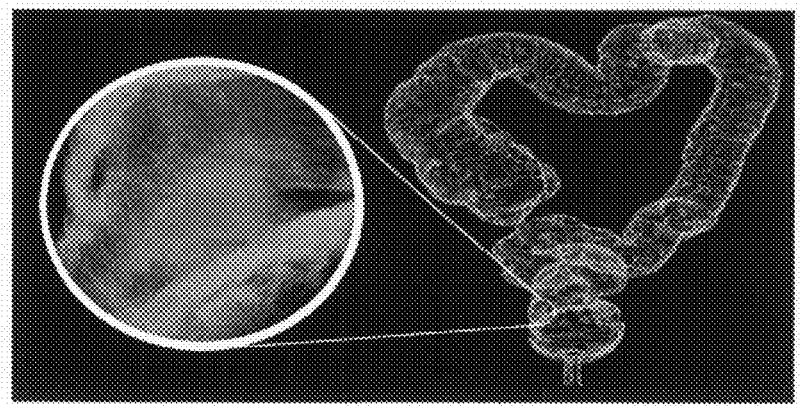
FIG. 27B
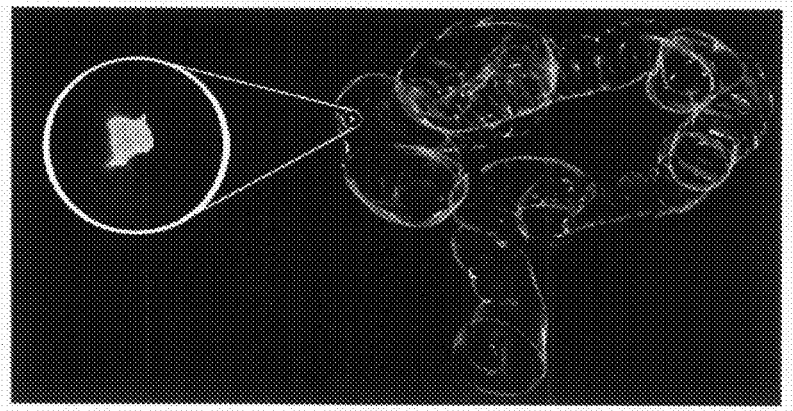
FIG. 27C
FIG. 27

SEGMENTING COLON WALL VIA LEVEL SET TECHNIQUES

TECHNICAL FIELD

The field relates to software analysis of images in a medical context.

BACKGROUND

Although colon cancer is the second leading cause of cancer death in the United States, it is also often treatable. Early detection of colon polyps is a key to treatment. CT colonography (CTC), also known as virtual colonoscopy, is a promising new non-intrusive detection technique where polyps are identified from computed tomography (CT) scans, sometimes with the aid of a computer-aided detection (CAD) system.

While the inner boundary of the colon wall has often been the focus of previous colon segmentation work, detection of the colon wall outer boundary is often difficult due to the low contrast between CT attenuation values of the colon wall and the surrounding fat tissue.

Thus, more work is needed to better detect the colon wall outer boundary and otherwise improve virtual colonoscopy technologies.

SUMMARY

A digital representation for an anatomical structure can be processed via a level set technique to identify the colon outer wall boundary. For example, the colon wall outer boundary can be segmented.

A speed image for the level set technique can be generated from a segmentation of the colon wall inner boundary. For example, the speed image can be generated via a gradient along a vector (e.g., perpendicular to the colon wall inner boundary) in a digital representation for a colon. The speed image can be used during level set processing to identify the colon wall outer boundary.

The segmented colon wall outer boundary can be used for a variety of purposes. For example, colon wall thickness can be determined. Colon wall thickness can be used in polyp candidate identification and classification, and diagnosis of colonic diseases (e.g., detection of diverticular disease). Other uses of the segmented colon wall include spasm detection, cancer detection, colon centerline determination, and fly throughs.

Additional features and advantages of the technologies described herein will be made apparent from the following detailed description of illustrated embodiments, which proceeds with reference to the accompanying drawings.

BRIEF DESCRIPTION OF THE DRAWINGS

The patent or application file contains at least one drawing executed in color. Copies of this patent or patent application publication with color drawings will be provided by the Office upon request and payment of the necessary fee. FIGS. 16-22, 24-30, and 33-35 are executed in color.

FIG. 16 shows a representation of a colon with a cutting plane showing segmentation of the lumen and outer colon wall.

FIG. 17 is a two-dimensional CT image slice showing superimposed results of colon wall segmentation.

FIG. 18 is a two-dimensional CT image slice showing superimposed results of colon wall segmentation.

FIG. 19 is a two-dimensional CT image slice showing superimposed results of colon wall segmentation.

FIG. 20 is a detail of a two-dimensional CT image slice showing superimposed results of colon wall segmentation.

FIG. 21 is an exemplary calculated speed image used during level set segmentation of the colon outer wall.

FIG. 22 is a two-dimensional CT image slice showing superimposed results of colon wall segmentation via the speed image shown in FIG. 21.

FIGS. 24, 25, and 26 are illustrations of colons indicating thickness of colon wall determined via level set segmentation.

FIGS. 27A-C are illustrations of colons indicating thickness of colon wall determined via level set segmentation with regions of interest therein shown in respective insets.

FIGS. 28, 29, and 30 are illustrations of colon cross sections indicating polyp detections based on colon wall thickness determined via level set segmentation.

FIG. 33 is a slice of a CTC scan showing segmentation of the colon wall.

FIG. 34 is a slice of a CTC scan showing the sigmoid portion of a colon with diverticular disease.

FIG. 35 is a slice of a CTC scan showing the sigmoid portion of another colon with diverticular disease.

DETAILED DESCRIPTION

Overview of Technologies

Figure 1:
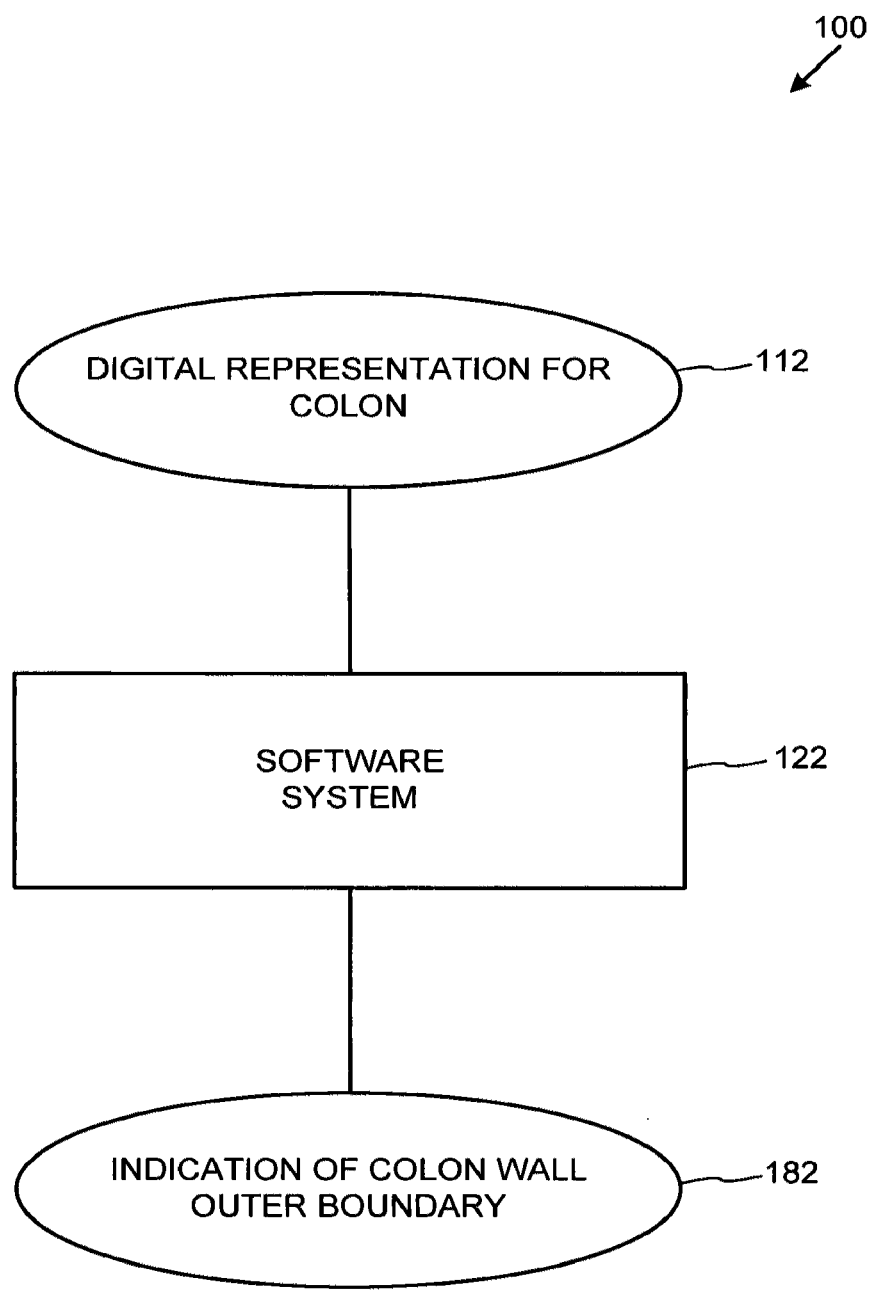
FIG. 1 is a block diagram of an exemplary system configured to process a digital representation for a colon and output an indication of a colon wall outer boundary via a level set technique.

The technologies described herein can be used in any of a variety of scenarios in which identifying the colon wall is desired. For example, when performing computer-aided detection of polyps in a CT scan of the colon, colon wall thickness can be considered when identifying or classifying candidate polyps. Further, diseases of the colon can be diagnosed via colon wall thickness calculations. For example, diverticular disease can be detected. Still further, the technologies described herein can be used for colon spasm detection, colon cancer detection, colon centerline determination, and flythroughs.

A digital representation for an anatomical structure includes any digital representation of an anatomical structure (or portion thereof) stored for processing in a digital computer. For example, representations can include two- or three-dimensional representations (e.g., one or more images) of portions of an anatomical structure stored via a variety of data structures. Representations can be composed of pixels, voxels, or other elements. A digital representation of an anatomical structure is sometimes called "virtual" (e.g., a "virtual colon") because it is a digital representation that can be analyzed to learn about the represented anatomical structure.

A component of a digital representation includes any two- or three-dimensional element that composes a part of a representation of a portion of an anatomical structure stored as an image. For example, pixels and voxels can be components.

Segmentation includes the process of dividing a digital representation for an anatomical structure into constituent parts into which a body, entity, or quantity is divided or marked off by or as if by natural boundaries. Thus, segmentation can include identifying the boundaries of an anatomical structure. Segmentation can include identifying the colon wall outer boundary. Further, segmentation can determine the location and extent of an anatomical structure or its boundary. For example, segmentation can indicate which portions of a digital representation are part of a colon wall, and which parts are not part of the colon wall. Types of segmentation include freehand segmentation, region-based (or region-growing) segmentation, fuzzy connectedness segmentation, K-means clustering segmentation, level set segmentation, active contours segmentation, expectation-maximization segmentation, and so on.

Imaging includes any technologies for obtaining an image of the inside of a body by transmitting electromagnetic or sonic waves through the body. Imaging includes radiographic images (with X-rays, for example computer tomography or "CT"), sonic energy (such as ultrasound) and magnetic fields (such as magnetic resonance imaging, or "MRI"). Although representations of an anatomical structure using such technology are sometimes called an "image," in practice, the representation can be a series of image slices (e.g., two-dimensional image slices stacked together to form a three-dimensional representation).

Exemplary anatomical structures in any of the examples herein include such structures as the colon, heart, bronchi, blood vessels, small bowel, biliary tract, urinary tract, and esophagus.

EXAMPLE 1

Exemplary System Outputting an Indication of Colon Wall Outer Boundary

FIG. 1 is a block diagram of an exemplary system 100 configured to process a digital representation for a colon and output an indication of a colon wall outer boundary via a level set technique. In the example, a digital representation 112 for a colon is processed by software 122 (e.g., employing a level set technique, such as any of the level set techniques described herein), which outputs an indication 182 of a colon wall outer boundary.

EXAMPLE 2

Exemplary Colon Wall

In any of the examples herein, the inner boundary of the colon wall can be a boundary between the colon wall and what is inside the colon (e.g., the lumen-mucosal boundary). The lumen boundary (e.g., boundary between the lumen and the colon) can be used as the colon wall inner boundary, and references to the lumen can imply the lumen boundary.

The outer boundary of the colon wall can be a boundary between the colon wall and what is outside the colon. For example, the outer boundary can be the colon serosal-tissue boundary, serosal soft-tissue boundary, serosal-fat boundary, serosal-organ boundary, serosal-serosal boundary (e.g., for two bowel loops that abut), or the like.

For the sake of convenience, sometimes the inner boundary of the colon wall is called the "inner wall," and the outer boundary of the colon wall is called the "outer wall," even though they can both be boundaries of a single colon wall.

Although the technologies described herein can be used to identify the entire colon wall for an entire colon, they can also be used to identify a colon wall for any portion of the colon (e.g., less than the entire colon, at a point on the colon, or the like).

An indication of a boundary of the colon wall can take a variety of forms. For example, the location and extent of the boundary can be indicated (e.g., as a set of pixels, voxels, or the like). The boundary can be of subvoxel accuracy, so the location can be indicated as a boundary not necessarily limited to discrete voxels. In practice, the boundary can be represented as a surface. For example, the outer boundary can be a surface, and the inner boundary can be a surface.

Segmentation of the colon wall can be accomplished by segmenting the inner colon wall boundary and the outer colon wall boundary. Given both boundaries, the location and extent of the colon wall can be determined as the space between the two boundaries. Two-dimensional (e.g., for image slices) or three-dimensional determinations (for a three-dimensional representation) can be made.

The outer boundary and inner boundary can also be considered together to calculate colon wall thickness. Again, thickness can be calculated for the entire colon or any portion of the colon (e.g., less than the entire colon, at a point on the colon, or the like).

EXAMPLE 3

Exemplary Subvoxel Accuracy

In any of the examples herein, subvoxel accuracy can be achieved. For example, a location for a wall boundary can be a point in three dimensional space that can refer to fractional voxels. Similarly, when a wall boundary is expressed as a surface, the surface can be indicated in units smaller than a single voxel (e.g., fractional voxels).

EXAMPLE 4

Figure 2:
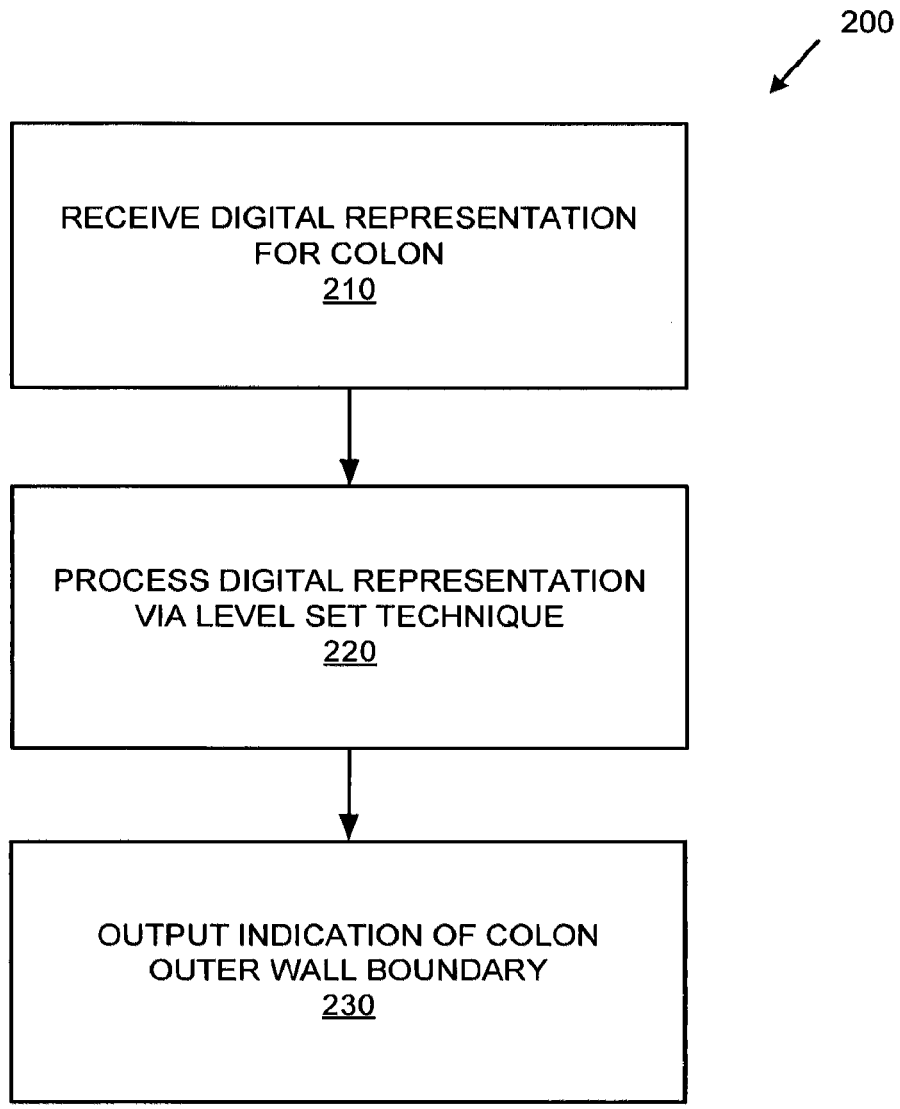
FIG. 2 is a flowchart of an exemplary method of processing a digital representation for a colon and outputting an indication of a colon outer wall boundary via a level set technique and can be implemented, for example, in a system such as that shown in FIG. 1.

Exemplary Method of Processing a Digital Representation for a Colon Via a Level Set Technique FIG. 2 is a flowchart of an exemplary method 200 of processing a digital representation for a colon and outputting an indication of a colon outer wall boundary via a level set technique and can be implemented, for example, in a system such as that shown in FIG. 1.

At 210, a digital representation for a colon is received. For example, any of the digital representations described herein can be used.

At 220, the digital representation is processed via a level set technique. For example, the colon outer wall boundary can be identified, segmented, or the like.

At 230, an indication of the colon outer wall boundary is outputted. For example, the indication of the colon outer wall boundary can be outputted to a user for observation (e.g., as a graphical representation). Or, the indication can be provided to other computer processing, which can further use the information (e.g., to calculate wall thickness and the like).

EXAMPLE 5

Exemplary Indication of Colon Wall Outer Boundary

In any of the examples herein, an indication of the colon wall outer boundary can take different forms. The indication of the colon wall outer boundary can take the form of a level set image. Or, the level set image can be used as an intermediate result from which a surface (e.g., an isocountour in the level set image representing the outer colon wall) is provided as an indication of the colon wall outer boundary. The indication can comprise a graphical representation (e.g., a displayed representation of) of the colon wall.

EXAMPLE 6

Exemplary Level Set Processing

In any of the examples herein, a level set technique can be used to identify, segment, or otherwise process an outer boundary for a colon wall. The level set technique can include level set processing. Level set techniques can evolve an isosurface in the direction of the surface normal. Evolution speed can depend on position, normal direction, curvature, shape, and the like. The isosurface can cross over the same point multiple times.

A general form of a level set method equation is as follows:

$$\frac{d}{dt}\psi = -\alpha \vec{A}(x) \cdot \nabla \psi - \beta P(x)|\nabla \psi| + \gamma Z(x)\kappa|\nabla \psi| \qquad (1)$$

where $\psi$ is the level set function, A is an advection term, P is a speed (e.g., propagation) term, Z is a spatial modifier term for the mean curvature term $\kappa$, and $\alpha$, $\beta$, and $\gamma$ are weights which can determine the influence of the terms on the movement of the isosurface.

Another form is as follows:

$$\frac{d}{dt}\psi(x, t) = -\alpha \vec{A}(x) \cdot \nabla \psi(x, t) - \beta P(x)|\nabla \psi(x, t)| + \gamma Z(x)\kappa|\nabla \psi(x, t)| \qquad (2)$$

where $\psi(x, t)$ is the level set function at point x and time t, A is an advection term, P is a speed (e.g., propagation) term, Z is a spatial modifier term for the mean curvature term $\kappa$, and $\alpha$, $\beta$, and $\gamma$ are weights which can determine the influence of the terms on the movement of the isosurface.

Level set techniques can be used to segment objects in the presence of noise and incomplete information, with the result defining the object boundary at subvoxel accuracy. The method can result in an image that contains positive level set values within the object and negative level set values external to the object from which the colon boundaries can be interpolated.

A general level set method can be applied during segmentation of both the inner and outer walls from CT virtual colonoscopy scans. Due to the contrast difference between the colon wall and lumen, a threshold level set segmentation method (e.g., based only on a lower and upper threshold value for the propagation term) can be used for a subvoxel accurate lumen segmentation.

To determine the colon outer wall boundary, a more complex geodesic active contour level set method (e.g., having an advection term that attracts the level set to the object's boundary) can be used.

EXAMPLE 7

Figure 3:
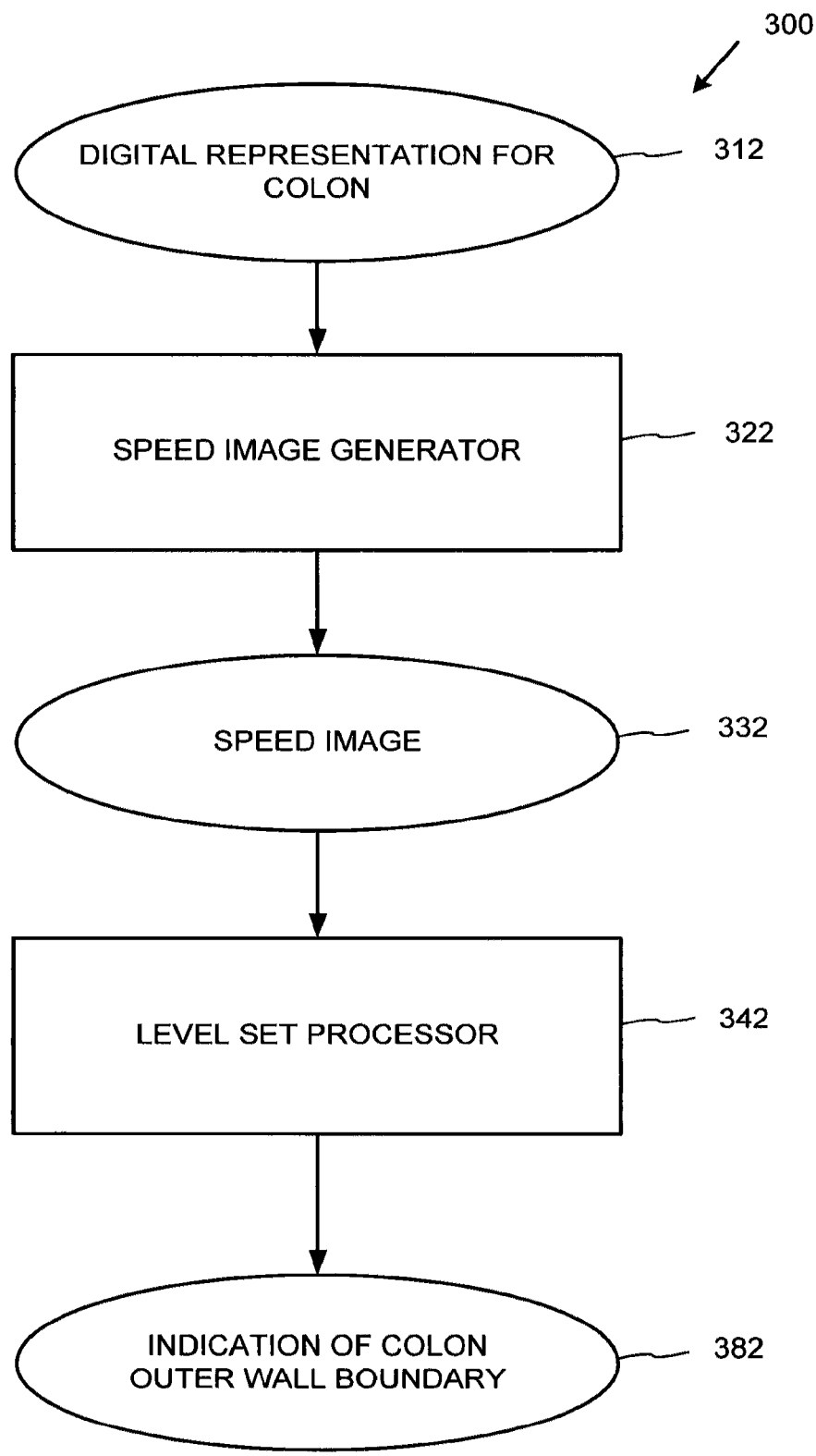
FIG. 3 is a block diagram of an exemplary system configured to process a digital representation for a colon and output an indication of a colon outer wall boundary via a speed image.

Exemplary System Outputting an Indication of a Colon Outer Wall Boundary Via a Speed Image FIG. 3 is a block diagram of an exemplary system 300 configured to process a digital representation for a colon and output an indication of a colon outer wall boundary via a speed image.

In the example, a digital representation 312 for a colon is input for a speed image generator 322, which is configured to generate a speed image 332 using any of the techniques described herein.

The speed image 332 can be used by the level set processor 342 as a speed function during level set processing to output an indication 382 of the colon outer wall boundary using any of the techniques described herein.

EXAMPLE 8

Exemplary Speed Function

In any of the examples herein, a speed image can be used for a speed function (e.g., a speed term) during level set processing (e.g., to segment a colon wall, its boundary, or both). The speed image can correspond to the original digital representation (e.g., image) for the colon (e.g., in size, number of components, and the like). Thus, it can be a three-dimensional image corresponding to an original acquired three-dimensional CT image, or it can be derived from the original image using any of a variety of image processing methods.

The values for the speed image can be calculated as described herein to influence the evolution of the level sets on the original image. Thus, the speed function term value for a location in the colon at a voxel can be the corresponding value (e.g., intensity) for the voxel in the speed image.

For example, intensity values in the speed image can be calculated as values that encourage or discourage the advance of the level set (e.g., an isosurface). Thus, during segmentation via level set processing with a speed function, the speed image can control the location in the original image at which boundaries are identified. For example, high intensity values can discourage evolution of the isosurface, and lower values can encourage isosurface evolution.

EXAMPLE 9

Figure 4:
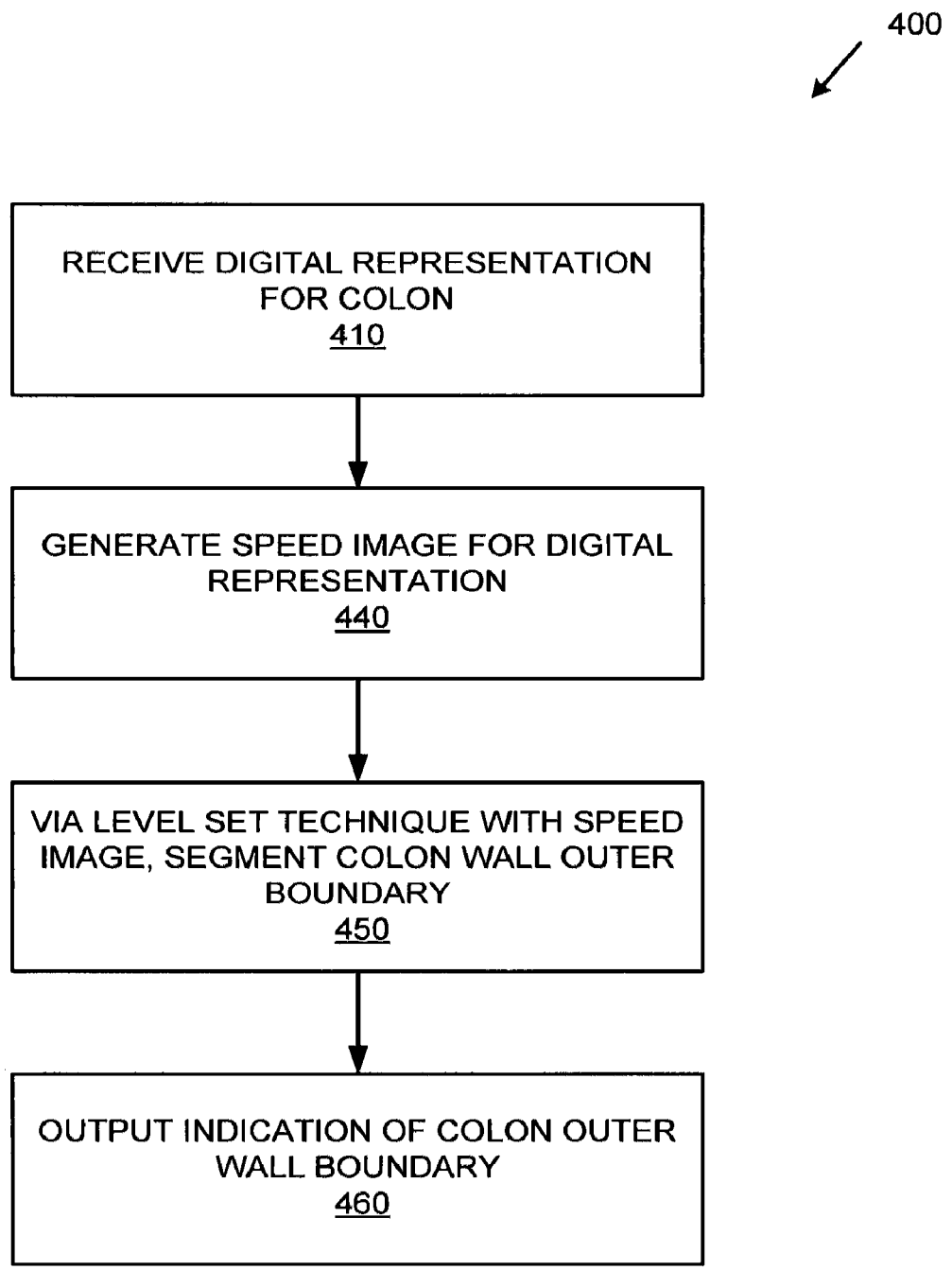
FIG. 4 is a flowchart of an exemplary method of processing a digital representation for a colon via a level set technique with a speed image and outputting an indication of a colon outer wall boundary.

Exemplary Method of Processing a Digital Representation for a Colon Via a Level Set Technique with a Speed Image FIG. 4 is a flowchart of an exemplary method 400 of processing a digital representation for a colon via a level set technique with a speed image and outputting an indication of a colon outer wall boundary.

At 410 a digital representation for a colon is received.

At 440, a speed image for the digital representation is generated.

At 450, the colon wall outer boundary is segmented via a level set technique (e.g., any of the level set processing described herein). Evolution speed of the isosurface can be proceed as indicated in the speed image.

At 460, an indication of the colon outer wall boundary is outputted. For example, an isocontour in the resulting level set image can represent the outer wall boundary of the colon.

EXAMPLE 10

Exemplary System Outputting Colon Wall Thickness

Figure 5:
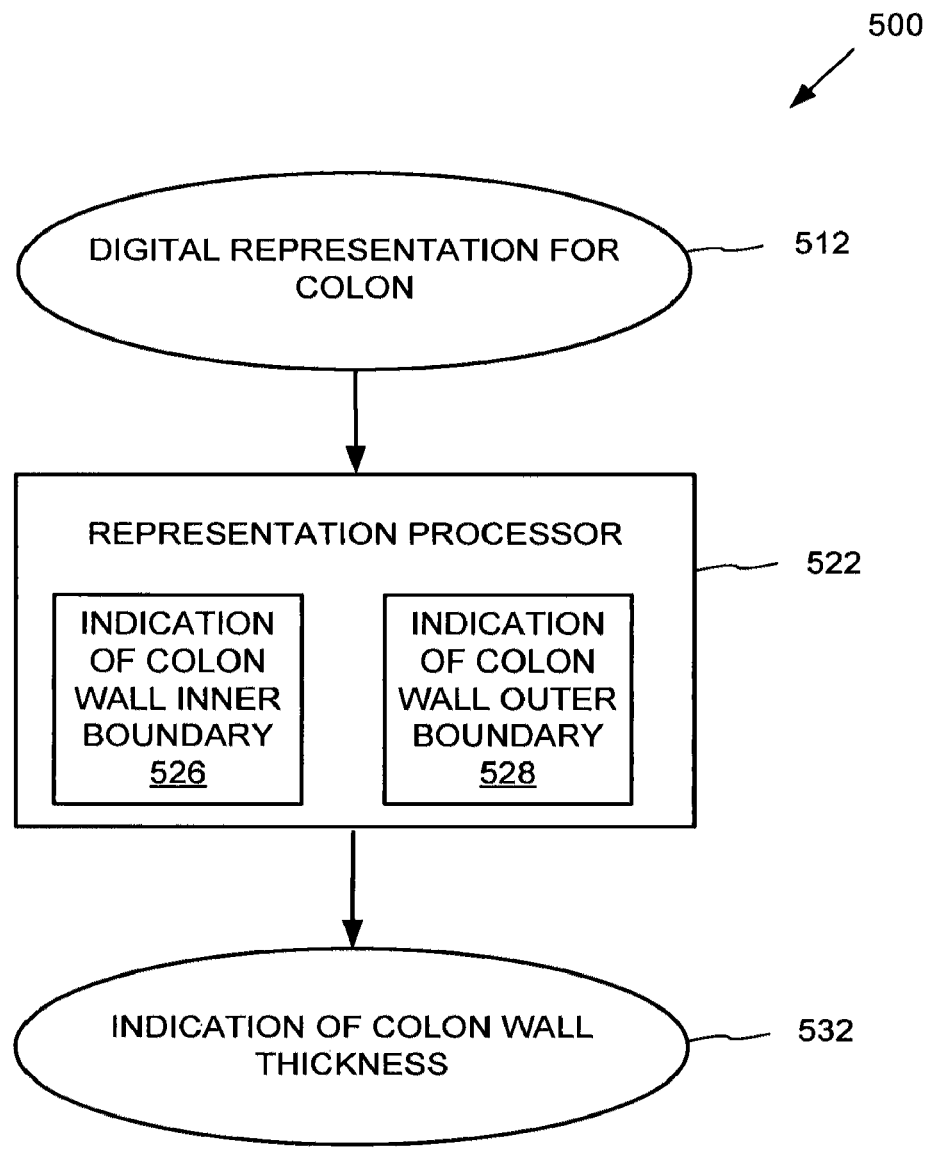
FIG. 5 is a block diagram of an exemplary system configured to process a digital representation for a colon and output an indication of colon wall thickness therefrom.

FIG. 5 is a block diagram of an exemplary system 500 configured to process a digital representation for a colon and output an indication of colon wall thickness therefrom.

A representation processor (e.g., colon wall segmentation tool) 522 is configured to receive a digital representation 512 for a colon as input. The representation processor 522 determines an indication 526 of the colon wall inner boundary and an indication 528 of the colon wall outer boundary (e.g., via any of the techniques described herein).

The representation processor 522 then outputs an indication of the colon wall thickness 532. For example, the distance between the boundaries can be calculated. The outer boundary of the colon wall and the inner boundary of the colon wall can be represented as surfaces. Distance between the surfaces can be determined. For example, the minimum distance between points on the inner colon surface and points on the outer colon surface can be found. For example, for a point on one (e.g., inner) wall surface (e.g., taken one at a time from points on the colon surface), the closest point on the other (e.g., outer) wall surface can be found. The thickness at the point on the wall surface is the distance between the two points. Such a technique can be repeated for other (e.g., remaining) points on the wall surface. Thickness can be expressed in millimeters or some other metric.

EXAMPLE 11

Exemplary Method of Outputting Colon Wall Thickness

Figure 6:
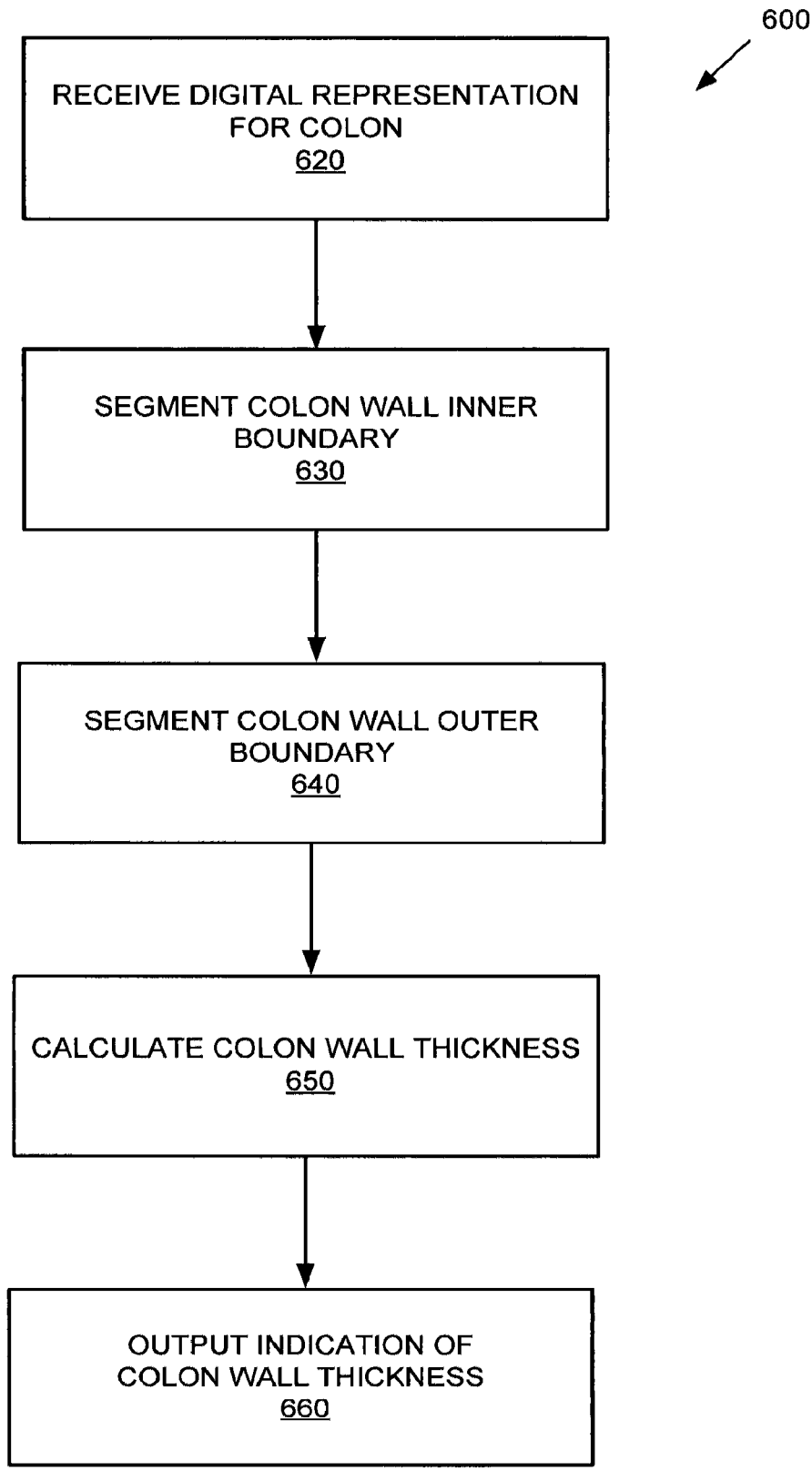
FIG. 6 is a flowchart of an exemplary method of processing a digital representation for a colon and outputting an indication of colon wall thickness therefrom.

FIG. 6 is a flowchart of an exemplary method 600 of processing a digital representation for a colon and outputting an indication of colon wall thickness therefrom.

At 620, a digital representation for a colon is received.

At 630, the colon wall inner boundary is segmented (e.g., via any of the techniques described herein).

At 640, the colon wall outer boundary is segmented (e.g., via any of the level set techniques described herein).

At 650, the colon wall thickness is calculated. For example, colon wall thickness can be calculated (e.g., measured for the virtual colon) at a particular point (e.g., the site of a polyp candidate), or at a plurality points. Measurements can be combined into a single value if desired (e.g., via averaging, median, or the like).

At 660, an indication of the colon wall thickness is outputted. For example, the thickness can be outputted for processing by software (e.g., a polyp candidate classifier) or outputted to a user interface for processing by a human user who can evaluate the thickness. The indication can be in size units (e.g., millimeters, tenths of millimeters, or the like).

EXAMPLE 12

Exemplary System Generating a Speed Image

Figure 7:
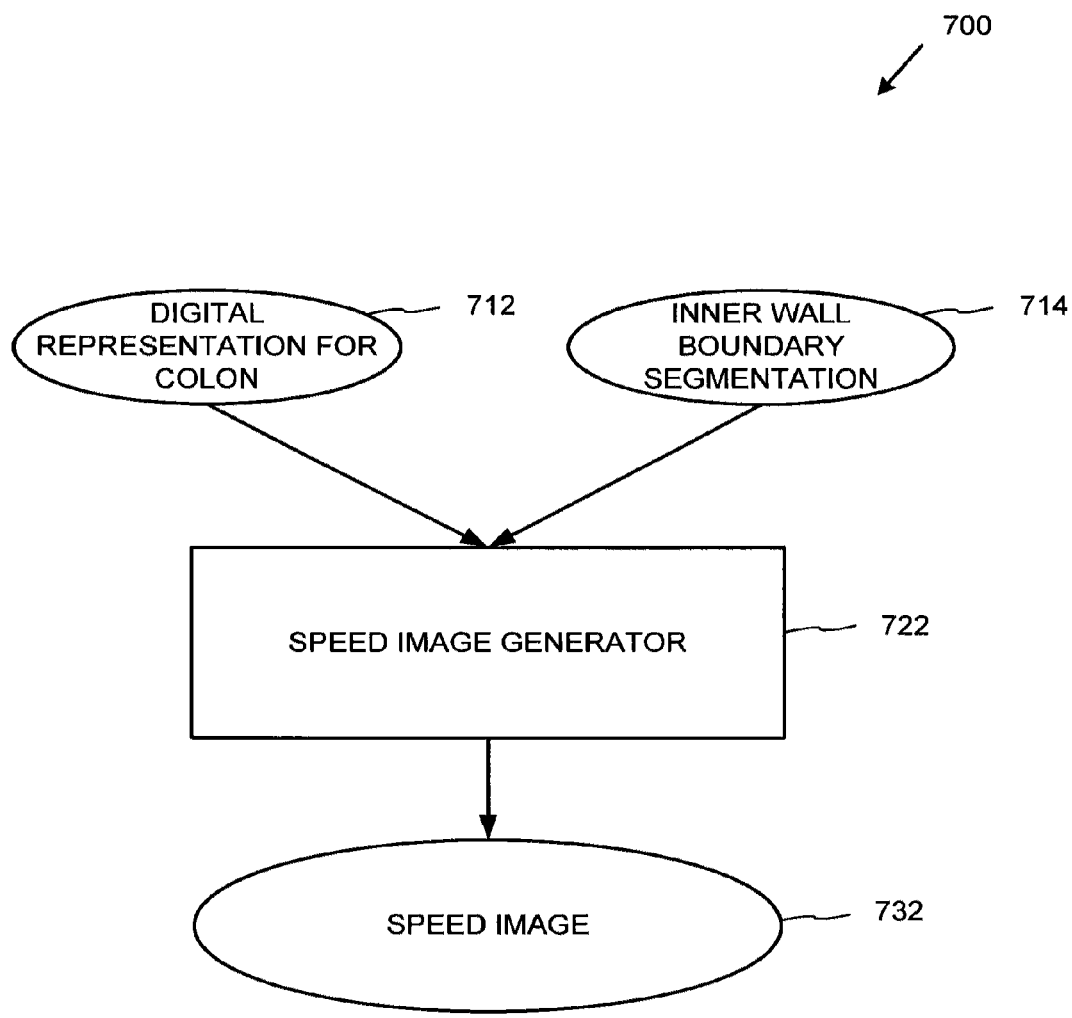
FIG. 7 is a block diagram of an exemplary system configured to process a digital representation for a colon and an inner wall boundary segmentation to generate a speed image.

FIG. 7 is a block diagram of an exemplary system 700 configured to process a digital representation for a colon and an inner wall boundary segmentation to generate a speed image.

In the example, a digital representation 712 for a colon and an inner wall boundary segmentation 714 are received by a speed image generator 722, which generates a speed image 732, which can be used in any of the examples herein.

EXAMPLE 13

Exemplary Method of Generating a Speed Image

Figure 8:
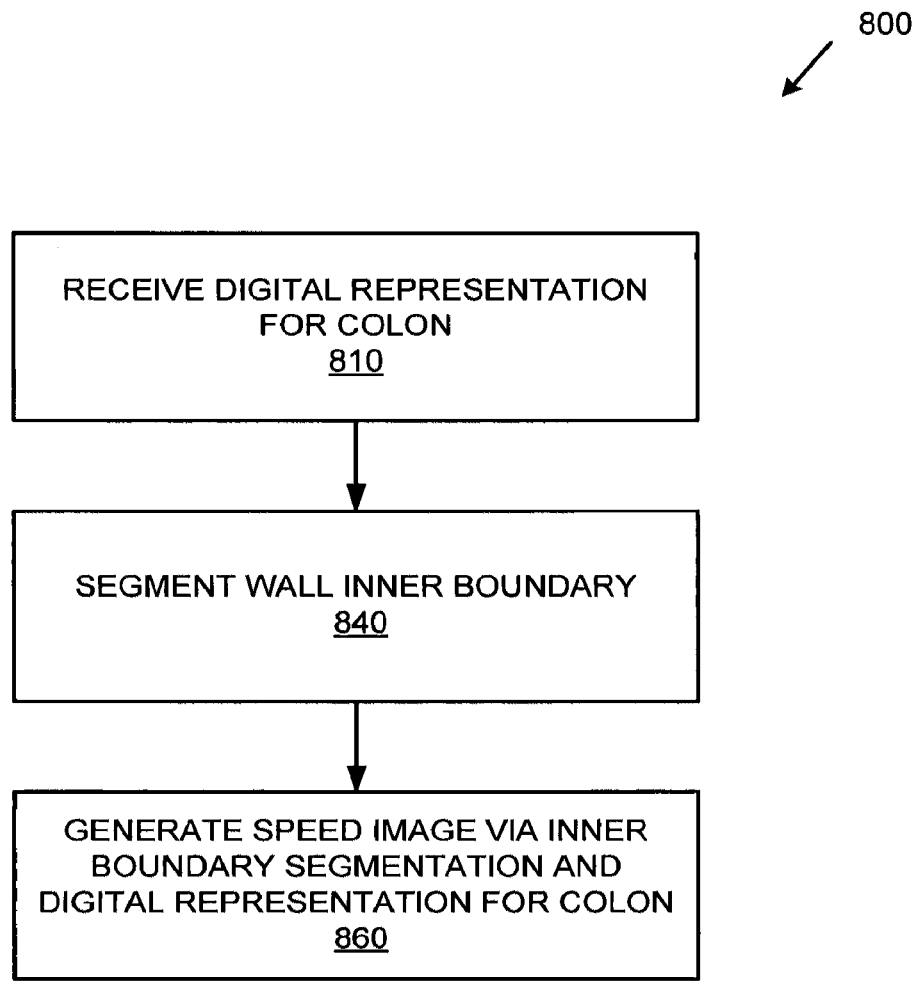
FIG. 8 is a flowchart of an exemplary method of generating a speed image from a digital representation for a colon and an inner wall boundary segmentation.

FIG. 8 is a flowchart of an exemplary method 800 of generating a speed image from a digital representation for a colon and an inner wall boundary segmentation and can be used in any of the examples herein.

At 810, a digital representation for a colon is received.

At 840, the colon wall inner boundary is segmented (e.g., via any of the techniques described herein).

At 860, a speed image is generated via the inner boundary segmentation and the digital representation for the colon (e.g., via any of the techniques described herein). For example, a derivative of intensity values for an image along a three-dimensional vector in the direction perpendicular to the colon wall inner boundary can be calculated. A sigmoid filter can be applied to the directional derivative image to invert the image and emphasize values for which the directional derivative is high. The value can be saved as an intensity value for the speed image at a location in the speed image corresponding to the location at which the derivative in the original image was calculated.

The resulting speed image can be used in any of the examples herein (e.g., when performing level set processing).

EXAMPLE 14

Exemplary Sigmoid Filter Techniques

In any of the examples herein, when generating a speed image, a sigmoid filter can be employed to invert the speed image after performing directional derivative computations. The filter can also suppress noise and emphasize high gradient values. Such high gradient values can reflect the outer wall boundary. Emphasizing the high gradient values can thus cause the level set to stop at the outer wall location (e.g., the inverted gradient value becomes zero). In practice, the sigmoid filter can set the speed image values to a base level except for the high gradient values.

EXAMPLE 15

Exemplary System Generating Colon Wall Outer Boundary

Figure 9:
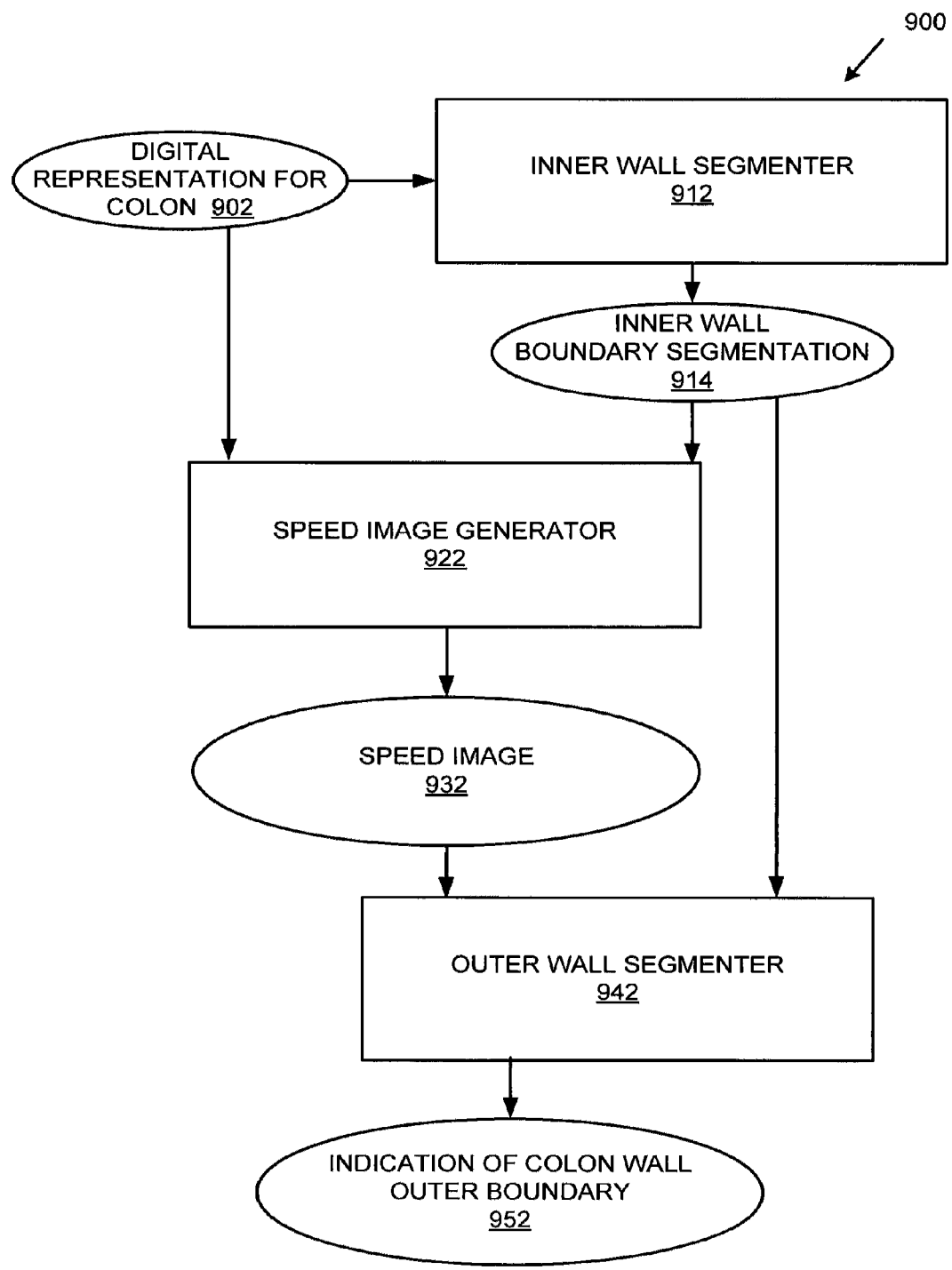
FIG. 9 is a block diagram of an exemplary system configured to process a digital representation for a colon and generate an indication of a colon wall outer boundary.

FIG. 9 is a block diagram of an exemplary system 900 configured to process a digital representation for a colon and generate an indication of a colon wall outer boundary and can be used in any of the examples herein.

In the example, a speed image generator 922 is configured to accept input as a digital representation 902 for a colon and an inner wall boundary segmentation 914, which is generated by the inner wall segmenter 912.

The speed image generator 922 is configured to generate a speed image 932 based at least on the digital representation 902 and the segmentation 914.

The outer wall segmenter 942 is configured to generate an indication 952 of a colon wall outer boundary based at least on the speed image 932 and the inner wall boundary segmentation 914.

EXAMPLE 16

Exemplary Method of Generating Colon Wall Outer Boundary

Figure 10:
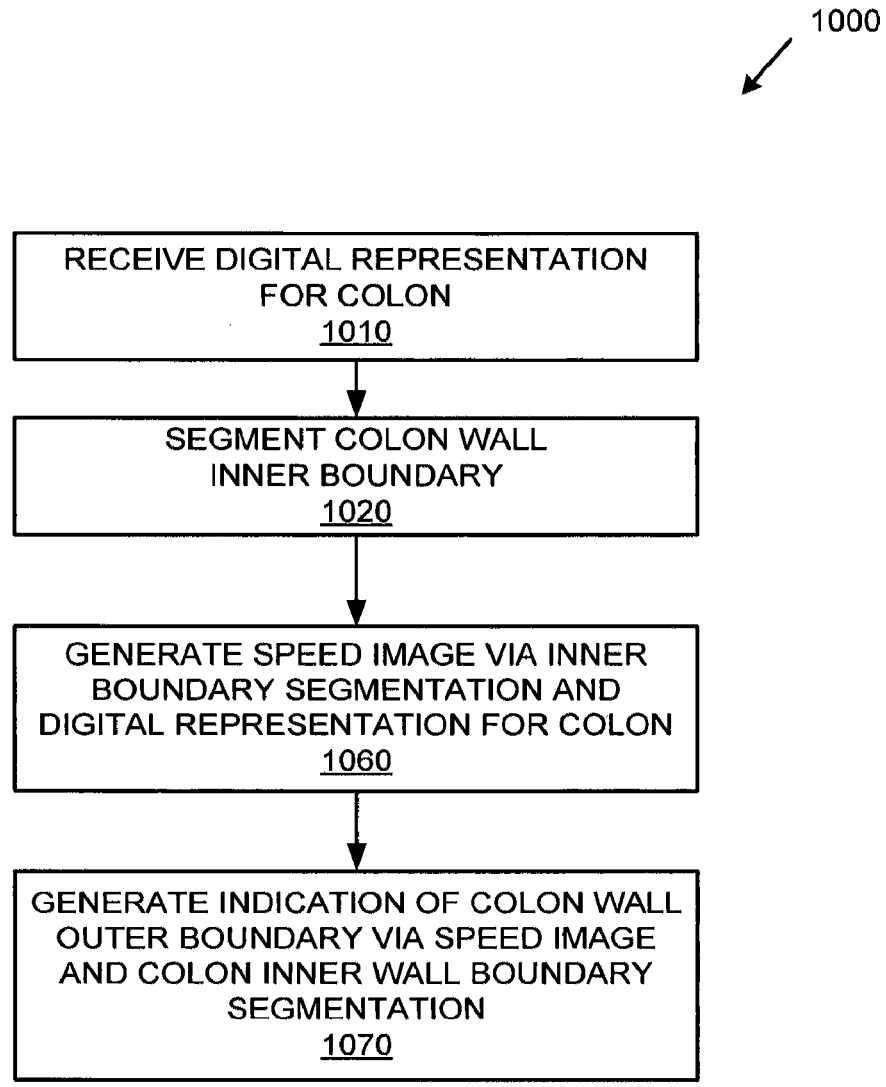
FIG. 10 is a flowchart of an exemplary method of generating an indication of a colon wall boundary via a speed image and a colon inner wall boundary segmentation.

FIG. 10 is a flowchart of an exemplary method 1000 of generating an indication of a colon wall boundary via a speed image and a colon inner wall boundary segmentation and can be used in any of the examples herein.

At 1010, a digital representation for a colon is received.
At 1020, the colon wall inner boundary is segmented (e.g., via any of the techniques described herein).
At 1060, a speed image is generated via the inner boundary segmentation and a digital representation for the colon.
At 1070, an indication of the colon wall outer boundary is generated based at least on the speed image and the colon inner wall boundary segmentation via level set processing.

EXAMPLE 17

Exemplary Colon Wall

Figure 11:
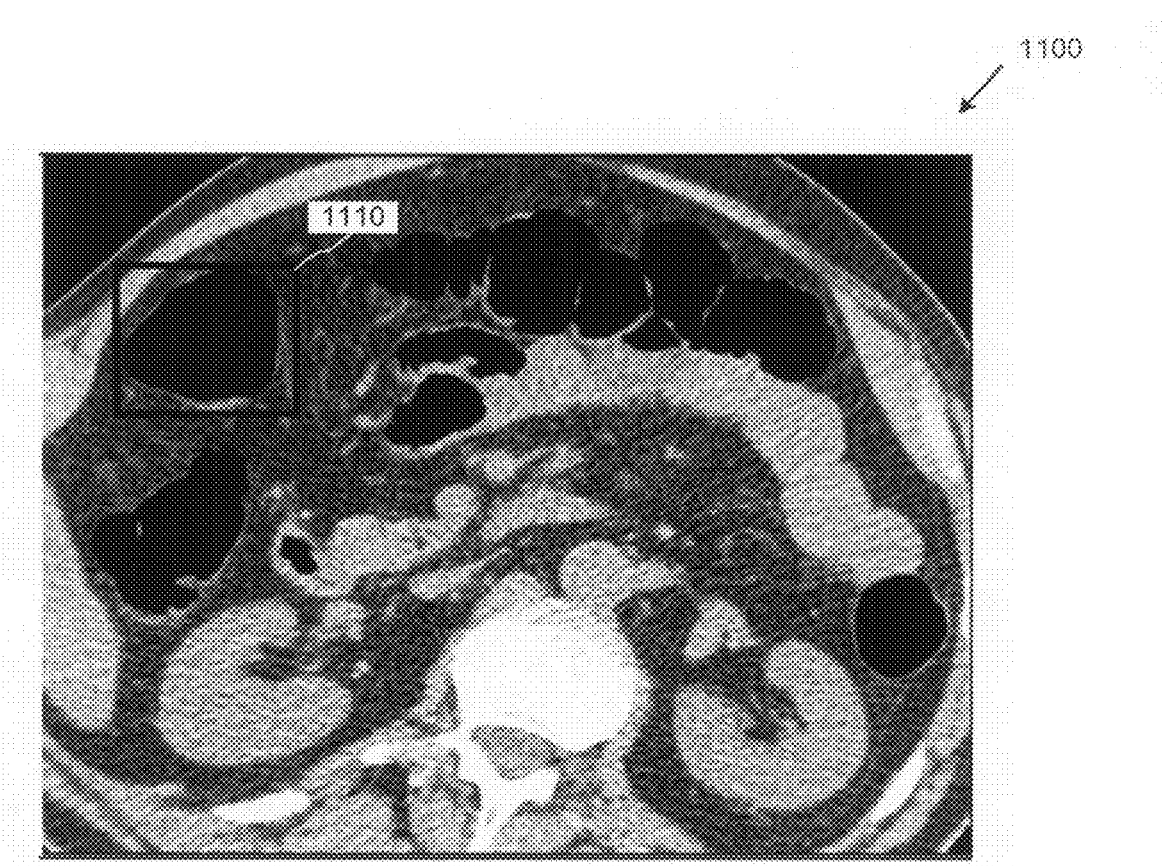
FIG. 11 is a two-dimensional CT image slice for a colon showing colon wall.

FIG. 11 is a two-dimensional CT image slice 1100 for a colon showing colon wall. The example includes various portions that have a colon wall. For example, a portion 1110 of the image slice includes a colon wall as described in detail in FIG. 12.

Figure 12:
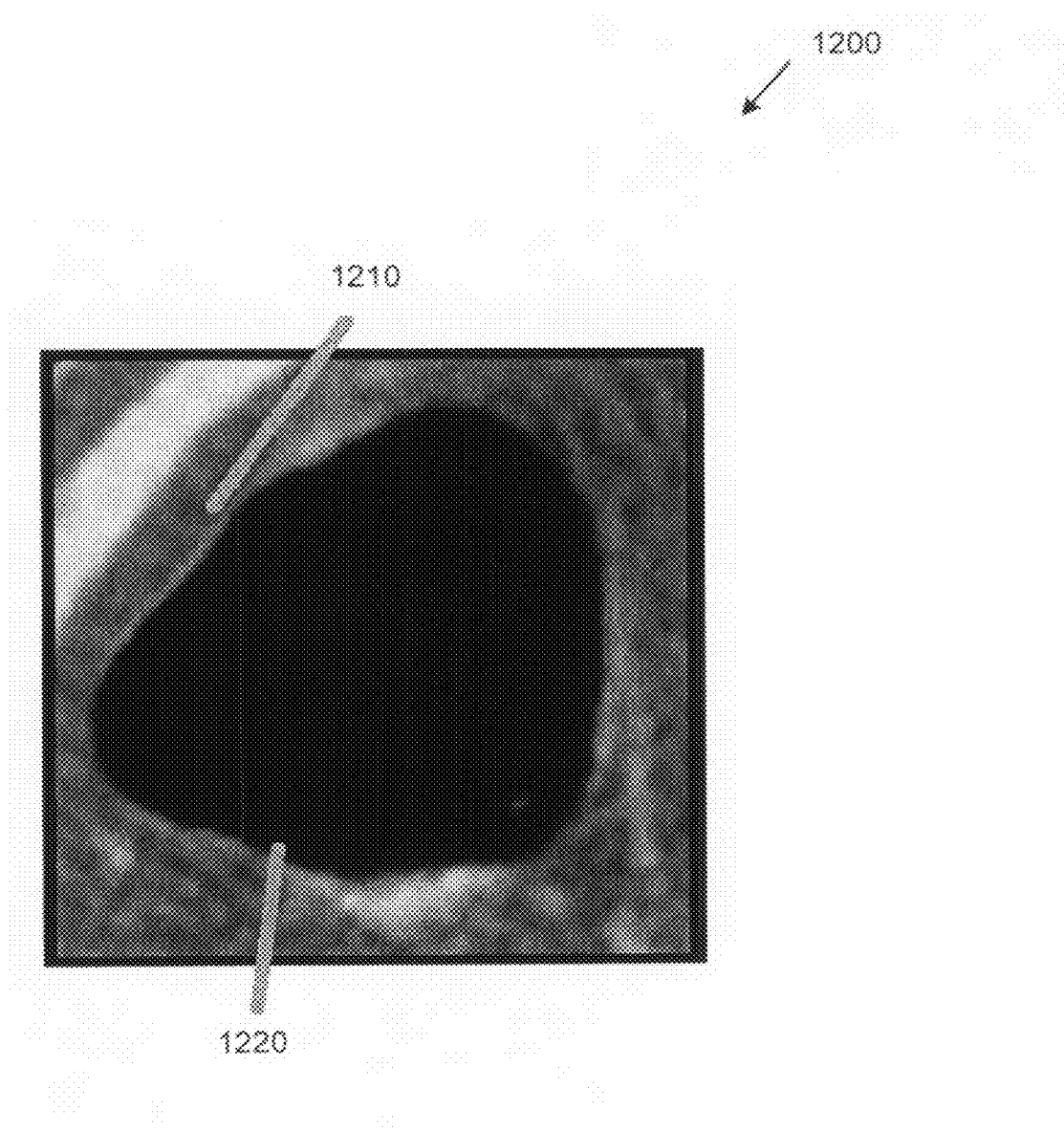
FIG. 12 is a detail of FIG. 11 showing the colon outer wall and low contrast between the colon outer wall and the surrounding tissue.

FIG. 12 is a detail 1200 of FIG. 11 showing the colon outer wall 1210 and low contrast between the colon outer wall 1210 and the surrounding tissue. The outer colon wall (e.g., serosal layer) 1210 and inner colon wall (e.g., mucosal layer) 1220 are indicated on the detail 1200.

EXAMPLE 18

Exemplary Lumen Segmentation

In any of the examples herein, the lumen can be segmented. The lumen boundary can be used as (e.g., be the same as) the colon inner wall. Thus, lumen segmentation can be used as the colon wall inner boundary segmentation.

The inner boundary can be useful when segmenting the colon wall. For example, lumen segmentation can be used as a starting point for segmenting the colon outer wall. The inner wall can also be used in conjunction with the outer wall to determine wall thickness.

The lumen can be segmented in a variety of ways. For example, a level set technique can be used that allows for segmentation of both fluid and air filled regions of the colon. Such a technique is described in Franaszek et al., U.S. patent application Ser. No. 11/482,682, filed Jul. 6, 2006, which is hereby incorporated by reference herein.

The lumen can be segmented via segmentation that creates a colon surface. Lumen segmentation can be performed using a simple threshold region growing method; the large difference in CT attenuation values between air and colon wall tissue allows the use of threshold methods to distinguish between the two regions during the segmentation.

Another technique is to segment the lumen by combining threshold region growing with level set methods to result in a smooth subvoxel-accurate segmentation.

EXAMPLE 19

Exemplary Lumen Segmentation

Region Growing

A simple threshold region growing segmentation can use a threshold value (e.g., −500 HU, about −500 HU, or the like) as the segmentation threshold for the lumen-colon inner wall boundary because it is the value which is half-way between air (i.e., −1000 HU) and soft tissue (i.e., about 0 HU). Such a segmentation results in a course lumen segmentation.

EXAMPLE 20

Exemplary Lumen Segmentation

Level Set

Figure 13:
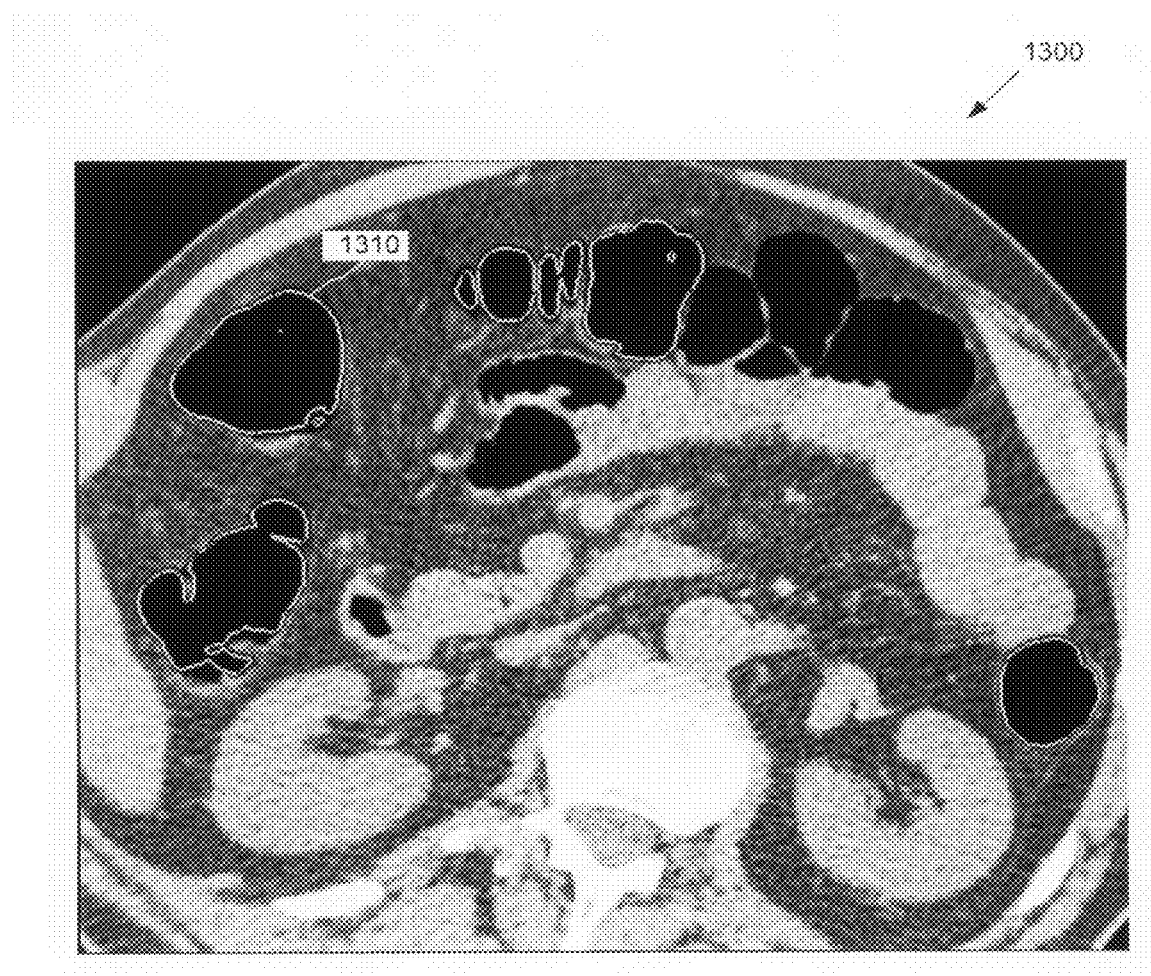
FIG. 13 is a two-dimensional CT image slice showing superimposed results of lumen segmentation.

A threshold level set technique for segmenting the lumen can use the threshold region growing segmentation as an initial level set boundary and a threshold value (e.g., −500 HU, about −500 HU, or the like) to determine a subvoxel-accurate segmentation of the colon lumen. FIG. 13 is a two-dimensional CT image slice 1300 showing superimposed results of lumen segmentation for an image (e.g., the image slice 1100 of FIG. 11) using such a technique.

In the example, the lumen (e.g., the colon wall inner boundary) segmentation results are shown as bright lines, such as the circular-like line 1310. In the example, subvoxel-accurate segmentation of the colon lumen was performed.

EXAMPLE 21

Exemplary Speed Function

In any of the examples herein, a speed function for the level set technique can be used during segmentation. A speed function can be represented by a speed image that the level set segmentation techniques use to determine whether the level set surface is to evolve and where it is to halt.

The speed image used in the outer wall level set segmentation can be calculated from both the lumen level set image and the original CT image. A three-dimensional directional derivative of the CT image can be performed in the direction perpendicular to the level sets produced by the lumen segmentation.

Figure 14:
FIG. 14 is a detail of a two-dimensional CT image slice showing superimposed level set isocontours from the lumen level set segmentation.

FIG. 14 is a detail 1400 of a two-dimensional CT image slice showing level set isocontours from the inner wall level set segmentation superimposed on the CT image values. The derivative of the image calculated in a direction perpendicular to the lumen level sets can be sigmoid inverted and used as a speed image for outer wall level set segmentation. The lumen boundary 1410A can be used as a starting point, from which the speed image is calculated as a three-dimensional derivative of the CT image in a direction perpendicular to the level set isocontours 1410A-F produced by the lumen segmentation. For example, a directed ray (e.g., vector) 1420 is drawn perpendicular to the level set isocontour 1410A in the example.

Figure 15:
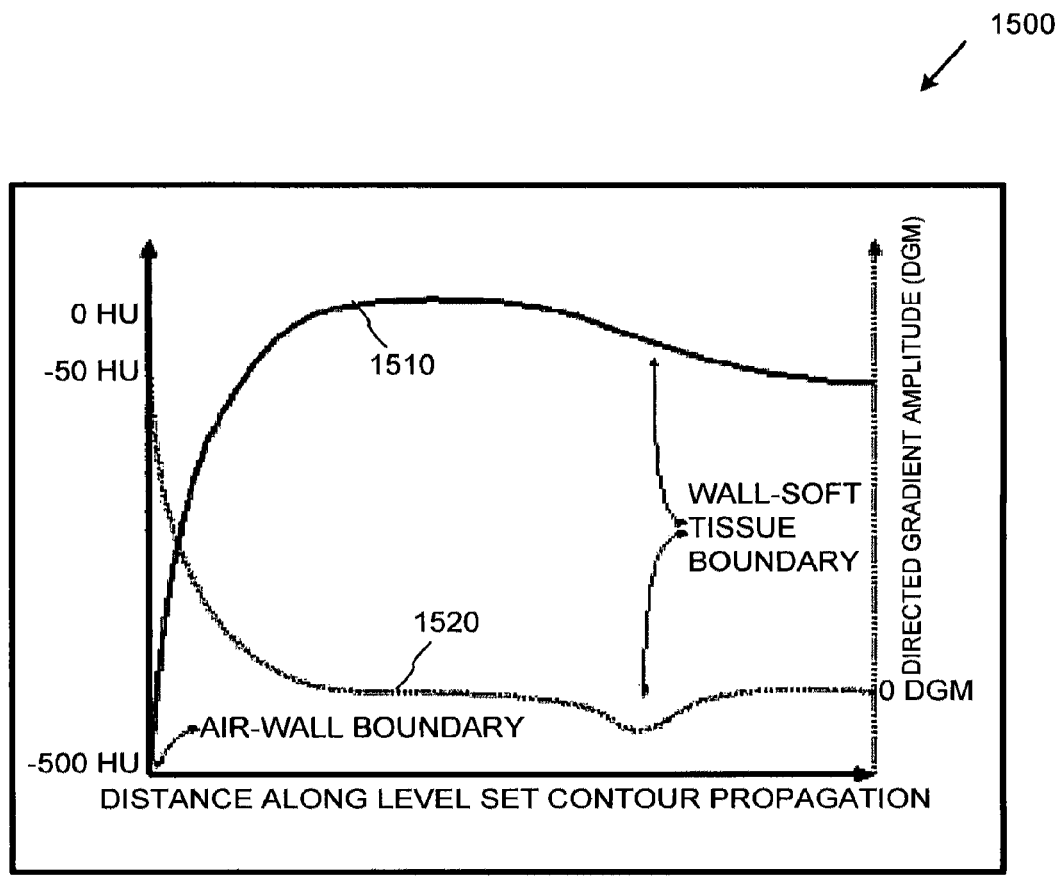
FIG. 15 is a graph showing an intensity profile of a CT image and gradient magnitude along a directed ray from the colon lumen to the outer wall.

FIG. 15 is a graph showing an intensity profile 1500 of a CT image and gradient magnitude along a directed ray from the colon lumen to the outer wall. In the example, the intensity profile of CT 1510 attenuation values (solid line) and gradient magnitude 1520 (dotted line) values along a directed ray (e.g., ray 1420 of FIG. 14) from the colon lumen to the other wall is shown.

The local non-maximum gradients along the level set expansion direction can be suppressed to further avoid the impact from noise and partial voluming effect from the lumen-colon wall boundary. A sigmoid filter can be used on the directional derivative image emphasizing the particular set of values where the directional derivative is high (e.g., where the outer colon wall boundary is located).

Inverting the output of the sigmoid filter allows a speed image to be created such that the level sets will propagate where there is a low directional gradient in the original CT image and stop when a high gradient along the colon outer wall is encountered.

EXAMPLE 22

Exemplary Colon Outer Wall Segmentation

In any of the examples herein, the level set segmentation of the colon outer wall can be computed via a three-dimensional geodesic active contour level set segmentation technique. The lumen level set segmentation can be used as the initial level set boundary, and the speed image can be calculated from the directional derivative of the original CT image (e.g., as described in Example 21).

The geodesic active contour level set segmentation technique can use an advection term that attracts the level set evolution to the high gradient values in the feature image and a curvature term that prevents the evolution of the boundary from exceeding a maximum curvature. The level set technique can adhere to near zero values (e.g., all near zero values) in the speed image and fill in the missing regions as desired, producing an outer wall segmentation that combines the confident location of boundaries seamlessly with desired boundaries. An isocontour (e.g., zero, two, or the like) in the resulting level set image can be used to represent the outer colon wall.

EXAMPLE 23

Exemplary Results

The technologies described herein were performed on three CT virtual colonoscopy scans each containing 512×512×512 images with a spacing of 0.7×0.7×1.0 mm$^3$. The colon wall in the scans consisted of various thicknesses throughout each colon segment. The results of performing the segmentation technologies on these cases is shown in FIG. 16-20; subvoxel-accurate segmentation of the colon wall was performed.

Figure 16:
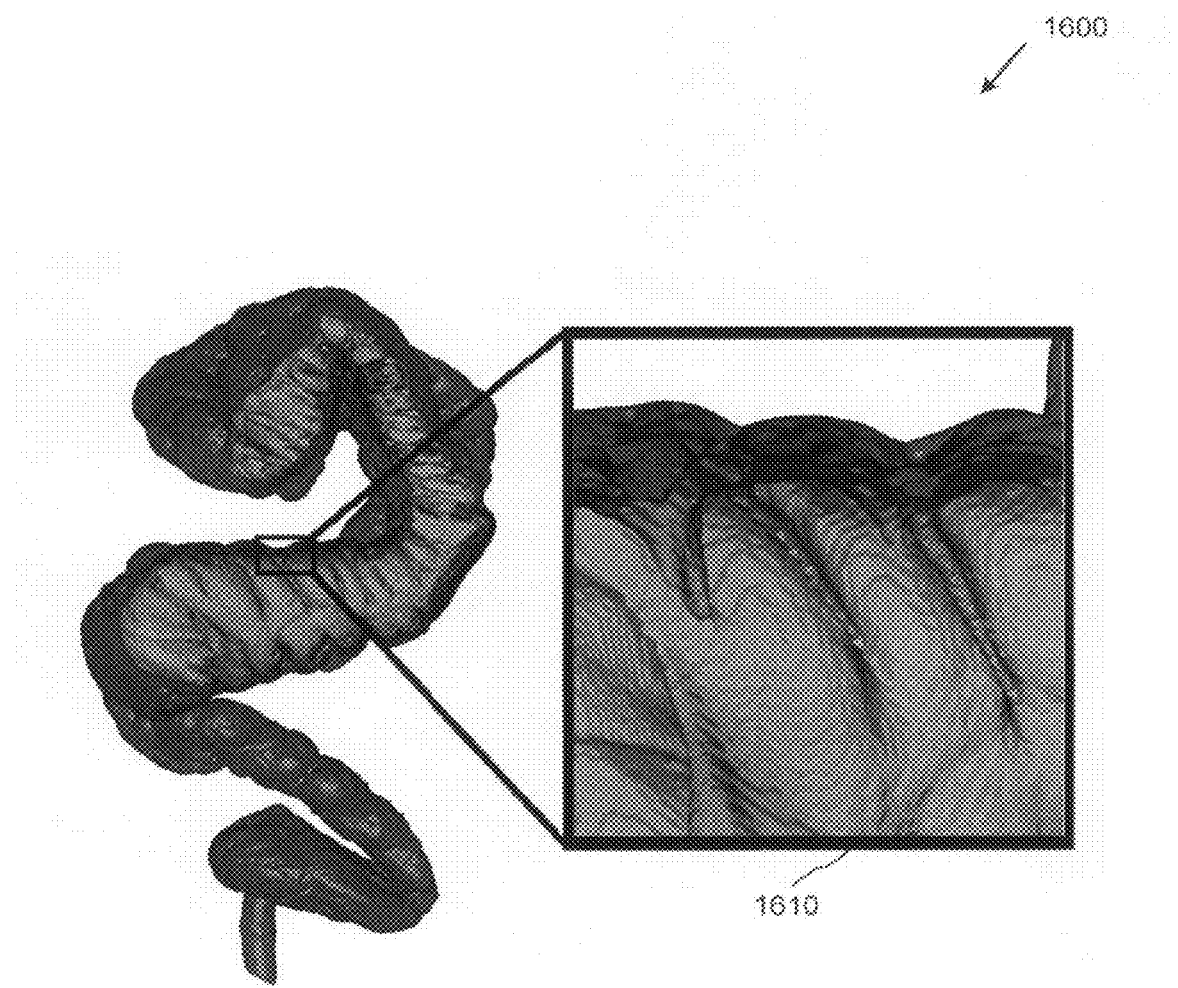

FIG. 16 shows a graphical representation 1600 of a colon with a cutting plane showing segmentation of the lumen (green) and outer colon wall (purple) as determined via the technologies described herein. A detail 1610 shows a close up view of the colon wall.

Figure 17:
Figure 18:
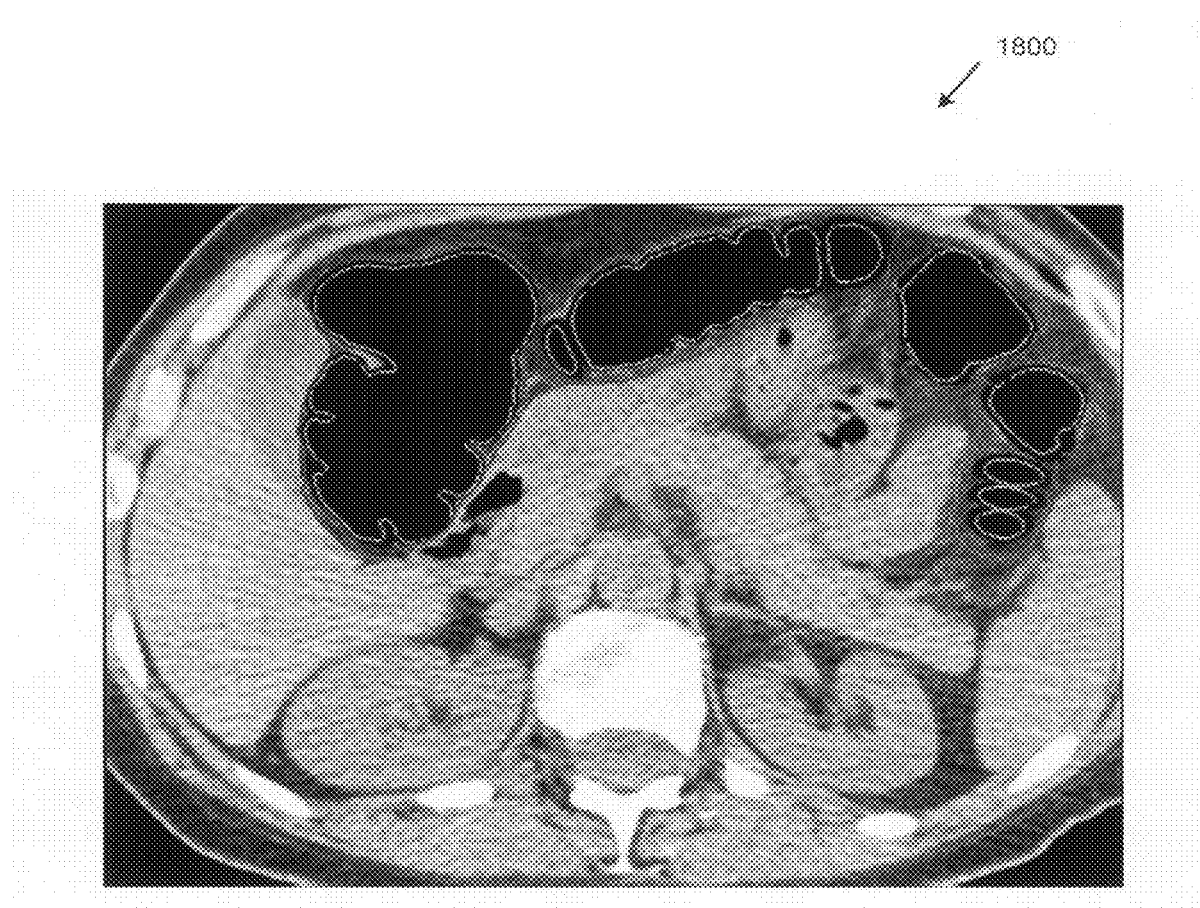
Figure 19:
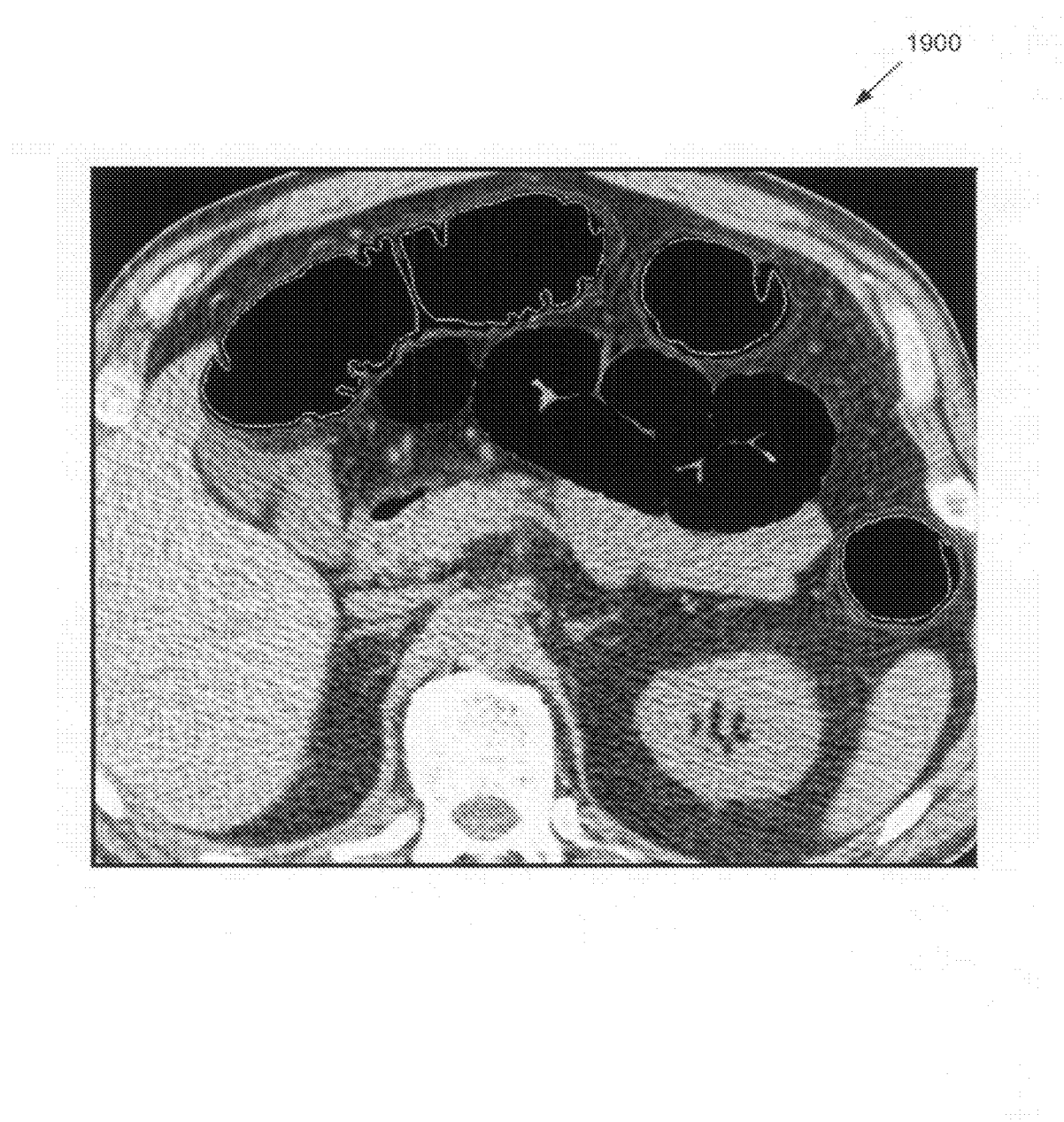

FIGS. 17, 18, and 19 show two-dimensional CT image slices 1700, 1800, and 1900 showing superimposed results of colon wall segmentation performed according to the technologies described herein. The colon inner wall boundary (e.g., as determined via the techniques described herein) is shown in green, and the colon outer wall (e.g., as determined via the techniques described herein) boundary is shown in red.

The accuracy of the segmentations was verified visually. The outer boundary of the colon wall was determined accurately, even though there was low contrast between the colon wall and the surrounding fat tissue. The technique can be fully automatic, thus requiring no user intervention.

Figure 20:
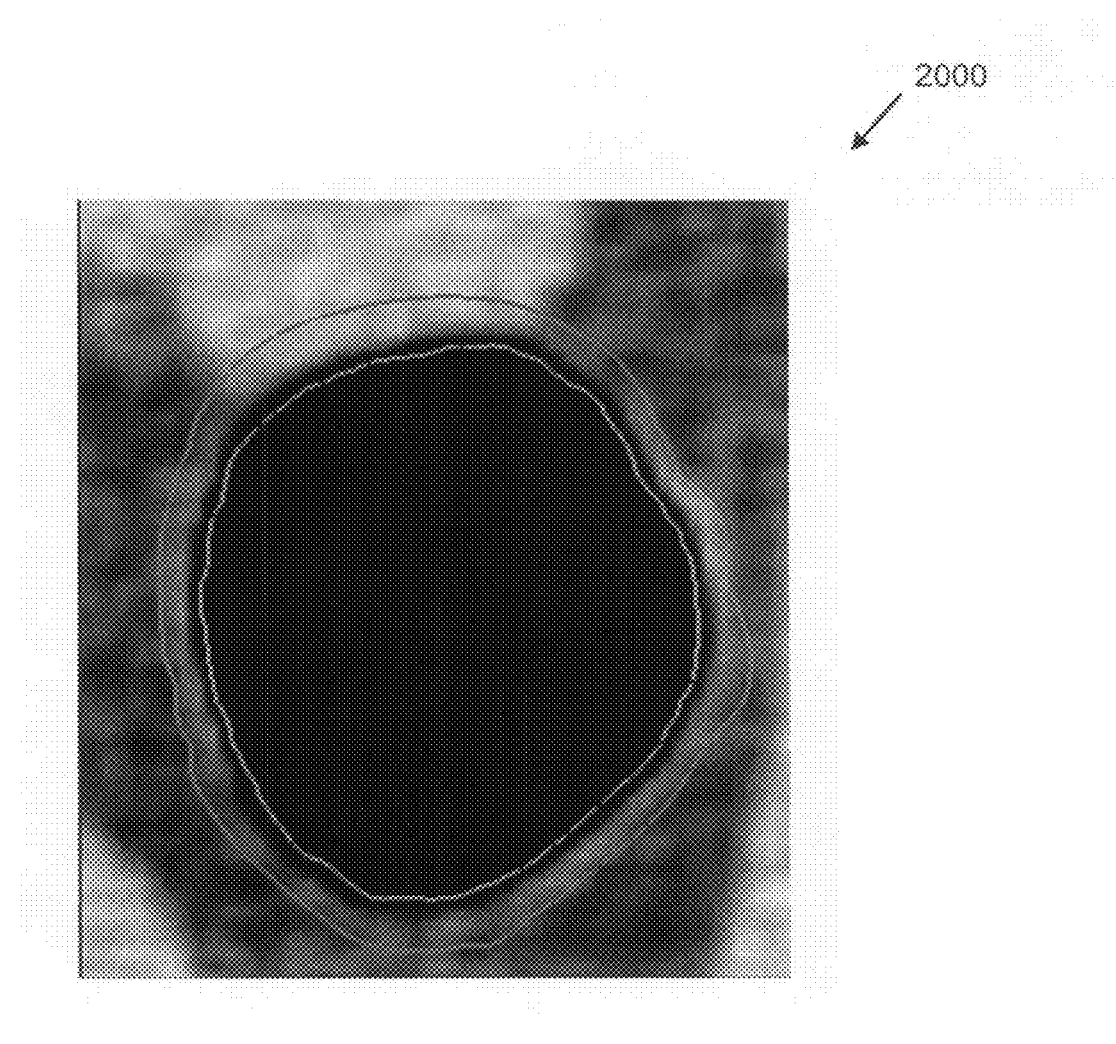

Even in areas where the colon is adjacent to other organs, the technologies can accurately find the colon outer wall, as shown in FIG. 20, which is a detail 2000 of a two-dimensional CT image slice showing superimposed results of colon wall segmentation performed according to the technologies described herein. The colon inner wall boundary is shown in green, and the colon outer wall boundary is shown in red. The detail 2000 shows an area of colon wall segmentation adjacent to small bowel in the upper portion of the detail 2000.

Using the derivative of the CT values along the direction perpendicular to the level set surfaces of the lumen segmentation allowed for an accurate detection of the colon outer wall. Further, the use of the geodesic level set method has allowed for a smooth subvoxel accurate colon wall segmentation to be performed.

When determining the position of the colon outer wall by starting at the lumen segmentation and considering the gradient direction relative to the lumen level set gradients, partial voluming effects between the colon lumen and wall can be avoided. Partial voluming effects cause difficulty in accurately segmenting the colon wall.

Also, finding the outer boundary within the lumen can be avoided if the technique is initialized with the lumen segmentation.

The resulting segmentation can contain the entire surface, rather than only several points on the outer colon boundary.

EXAMPLE 24

Exemplary Enhanced Level Set Techniques

In any of the examples herein, level set segmentation of the colon outer wall can be computed by using a three-dimensional geodesic active contour level set segmentation method.

A lumen level set segmentation can be used as the initial level set boundary, and the speed image can be calculated from a directional derivative of the original CT image. A three-dimensional derivative of the CT image can be performed in a direction perpendicular to the level sets produced by the lumen segmentation:

$$g(i) = \frac{k(i + \|v(i)\|) - k(i - \|v(i)\|)}{2} \quad (3)$$

where k(x) is the CT value at position x, and v(x) is the vector (e.g., the vector 1420 of FIG. 14) perpendicular to the segmentation level sets at position x.

The local non-maximum gradients along the level set expansion direction can be suppressed to avoid the impact from noise and partial voluming effects from the lumen-colon wall boundary by removing isolated pixels of high gradient magnitudes.

By using two sigmoid filters in series on the directional derivative image with an $\alpha=-4.0$, $\alpha=0.02$ and a $\beta=0.0$, $\beta=0.48$, respectively, both with min=0 and max=1, the particular set of values where the directional derivative is high (i.e., where the outer colon wall boundary is located) can be emphasized. Inverting the output of the sigmoid filter allows a speed image to be created such that the level sets will propagate where there is a low directional gradient in the original CT image and stop when a high gradient along the colon outer wall is encountered.

Figure 21:
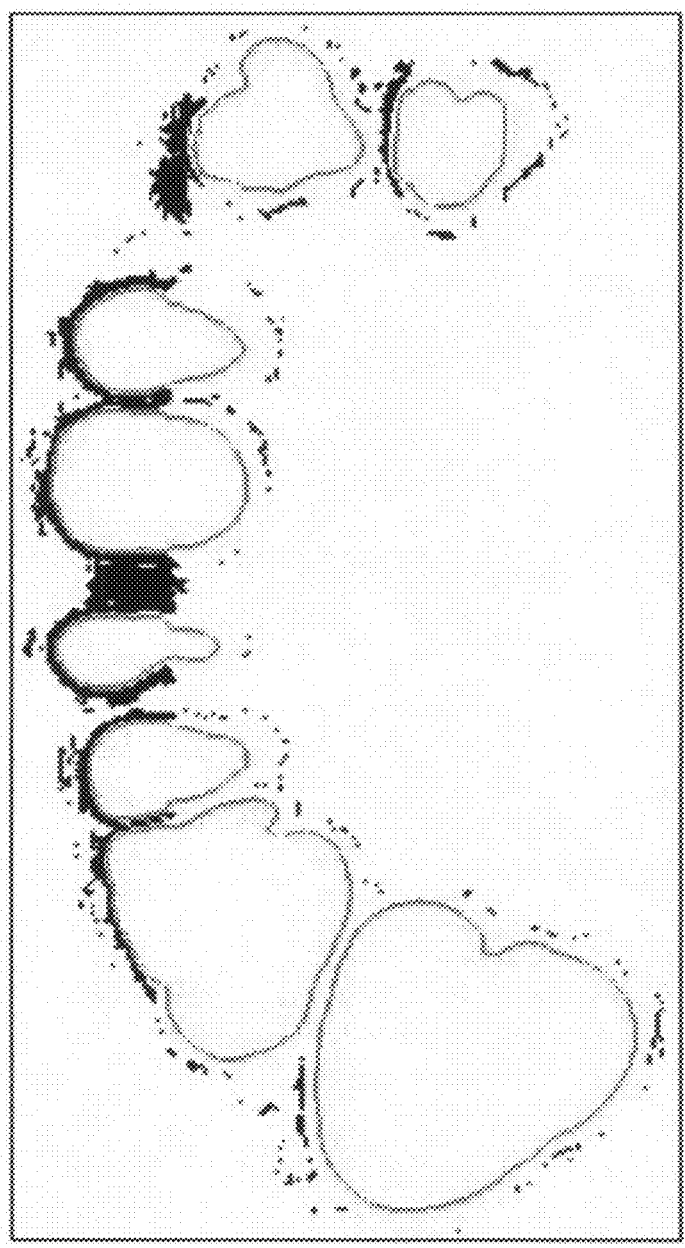

FIG. 21 shows an exemplary speed image 2100. The speed image can be used to determine the propagation of the geodesic active contour level set segmentation of the colon outer wall. White indicates high speeds of propagation, while black indicates zero speed of propagation. The colon inner boundary is shown in green.

The geodesic active contour level set segmentation can then be used along with the speed image to determine the location of the colon outer wall. This method can use Equation (2) with an advection term, $\alpha=0.3$, that attracts the level set evolution to the high gradient values in the feature image, a propagation term, $\beta=0.2$, that evolves the boundary outwards, and a curvature term, $\gamma=0.3$, that prevents the evolution of the boundary from exceeding a maximum curvature. The level set technique also adheres to near zero values (e.g., all near zero values) in the speed image and fills in the missing regions to produce a boundary as desired. The geodesic active contour level set segmentation method produces an outer wall segmentation that combines the confident location of boundaries seamlessly with the expected boundaries. The zero iso-surface in the resulting level set image can represent the outer colon wall.

Figure 22:

FIG. 22 is a two-dimensional CT image slice 2200 showing superimposed results of colon wall segmentation via the speed image shown in FIG. 21. The colon inner boundary (e.g., as determined via the techniques described herein) is shown in green, and the colon outer boundary (e.g., as determined via the techniques described herein) is shown in red.

EXAMPLE 25

Exemplary Outer Wall Segmentation

Figure 23:
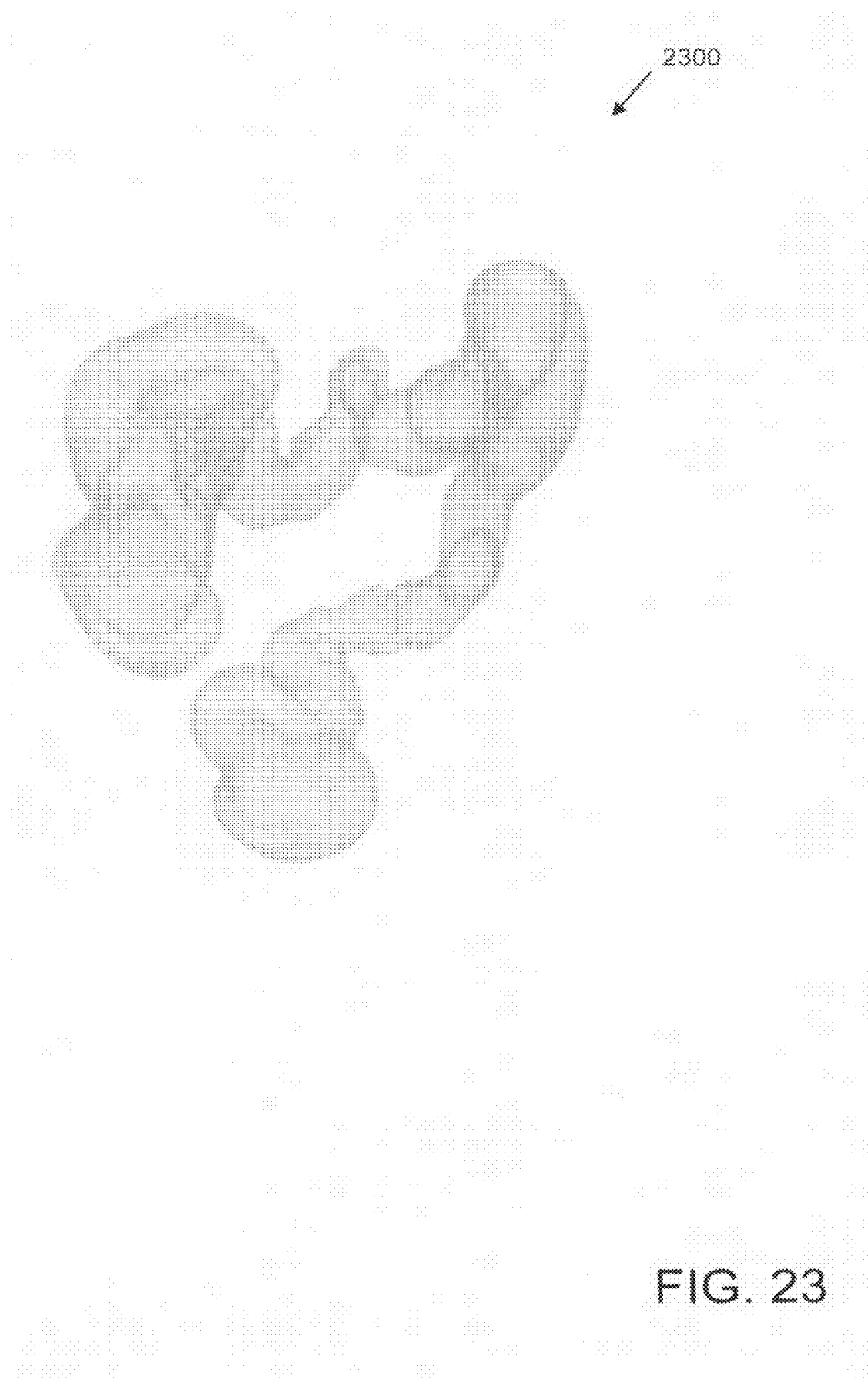
FIG. 23 is an illustration of a surface of an outer colon wall determined via level set segmentation.

FIG. 23 is an illustration of a surface 2300 of an outer colon wall determined via level set segmentation (e.g., using the inner wall segmentation as an initial surface for the colon's outer wall segmentation).

EXAMPLE 26

Exemplary Uses of Outer Wall Segmentation

In any of the examples herein, the outer wall segmentation can be useful for segmenting the colon wall and automatically determining its position, which can otherwise be difficult (e.g., because of the low contrast between CT attenuation values for the colon wall and the surrounding fat tissue). For example, colon wall thickness can be calculated using the outer wall segmentation in combination with the inner wall segmentation. So, colon wall thickness can be calculated automatically by software.

The wall thickness thus determined can have desirable properties, such as relatively smooth variation and decreased sensitivity to noise.

Further, segmenting the outer wall can be useful for identifying and classifying polyp candidates. For example, characteristics of the outer wall, colon wall thickness, or both can be included as an input feature when identifying or classifying polyp candidates.

Another use of the outer wall segmentation is identifying colonic diseases (e.g., muscular hypertrophy and diverticulitis), which can be diagnosed via colon wall thickness calculation results.

Still other uses are colon spasm detection, and colon cancer detection.

Still other uses include determining a colon centerline. The outer colon wall or the centerline can be used for determining a path for a fly through of the virtual colon (e.g., in portions of the colon which are insufficiently distended to allow for segmentation of the colonic inner wall).

By contrast, manual determination of the colon wall thickness can be very time consuming. In addition, it is often difficult to determine the precise location of the boundaries of the colon on two-dimensional slices due to partial voluming effects.

EXAMPLE 27

Exemplary Polyp Candidate Classifier

In any of the examples described herein, colon wall thickness can be inputted into a polyp candidate classifier configured to determine whether a polyp candidate is a true positive. For example, a software system can identify polyp candidates. A polyp candidate classifier can then classify the polyp candidates as true positives or false positives based on a plurality of features (e.g., characteristics) submitted to the polyp candidate classifier. The classifier can use the colon wall thickness calculations (e.g., based on level set segmentation of the colon wall) described herein as an input feature.

Such classifiers can be trained or otherwise developed based on training data with known results (e.g., polyp candidates classified by a human radiologist).

EXAMPLE 28

Exemplary Automatic Technologies

The technologies described herein can provide an automatic technique for determining a subvoxel-accurate segmentation of the colon wall. The technologies can result in appropriate segmentations when the colon wall is thick or thin. The resulting accurate segmentations of the colon wall can be useful for any of the applications described herein.

EXAMPLE 29

Exemplary User Interfaces

In any of the examples herein, graphical depiction of the colon wall or a portion thereof can be displayed to a human (e.g., radiologist), who decides what action, if any, to take. Such interfaces can allow manipulation of the graphical depiction, such as rotation, zooming, and the like.

The interface can highlight (e.g., zoom in on or depict in a special color) areas detected as unusual (e.g., having colon wall thickness outside of defined thresholds).

EXAMPLE 30

Exemplary Colon Thickness Calculation

After corresponding points on both the inner and outer surface are calculated, the Euclidean distance between the outer and inner surface at each potential polyp position can be calculated.

EXAMPLE 31

Exemplary Level Set Processing

A Laplacian level set method can be used to perform the lumen segmentation and results in a level set image that contains different level set isosurface values; the zero isosurface represents the lumen-colon wall boundary. Since the outer wall segmentation can use the lumen segmentation as the initial surface, the value of the level set function in the lumen segmentation image at any point is the distance from the point to the current front. Thus, for any point on the outer surface, the absolute value of the lumen segmentation level set field at the point is the level set distance from the point to the inner surface. A threshold on the distance can be used to remove areas where the colon wall thickness is low. The threshold can also simultaneously eliminate many folds from a list of potential polyps.

EXAMPLE 32

Exemplary Colon Thickness Map

In any of the examples herein, a thickness map between the inner and outer colon wall surfaces can be assembled from the calculated thicknesses. The map can be depicted visually by showing a graphic representation of the colon and using different colors to represent different thicknesses (e.g., one color for average thickness, another for above average, and another for below average). The colon wall thickness can be color mapped on the colon surface.

If desired, opacity for the average and below average colors can be varied to make the regions of interest (e.g., above average thickness) more visible.

EXAMPLE 33

Exemplary Clustering and Filtering

In any of the examples herein, after a thickness map of the colon has been calculated, the list of potential polyps can be further reduced by clustering candidate detections that are close to each other (e.g., within a threshold distance). For example, potential polyp voxels that are within n (e.g., two) voxels from each other can be grouped into the same polyp location. Also, detected points that have only n (e.g., one) voxels can be eliminated because such detections are most likely due to noise.

One technique for determining where a polyp is located is to use a threshold thickness. The thickness can also be used as one of a plurality of features of a more sophisticated classifier, such as a support vector machine or one or more neural networks. The classifier can be trained on known polyps.

EXAMPLE 34

Exemplary Colon Thickness Map Experiments

The level set techniques described herein for initial polyp detection was compared to a colonography CAD system that uses mean curvature, Gaussian curvature, and sphericity to detect potential polyps on the colon surface. The curvature and sphericity threshold parameter settings, which allow for the detection of elliptical shaped objects, were set to predetermined values. Polyp detections using the curvature based method that had only one point were eliminated from the list of potential polyp detections.

The technologies described herein were performed on three randomly chosen CT virtual colonoscopy scans with volume sizes between 512×512×354 to 512×512×424 images with a spacing of 0.7×0.7×1.0 mm$^3$. Each colon contained one polyp, which had a size of 1.5 cm, 2.0 cm, and 1.0 cm, respectively. The colon wall in the scans had various thicknesses throughout the colon segments.

Figure 24:
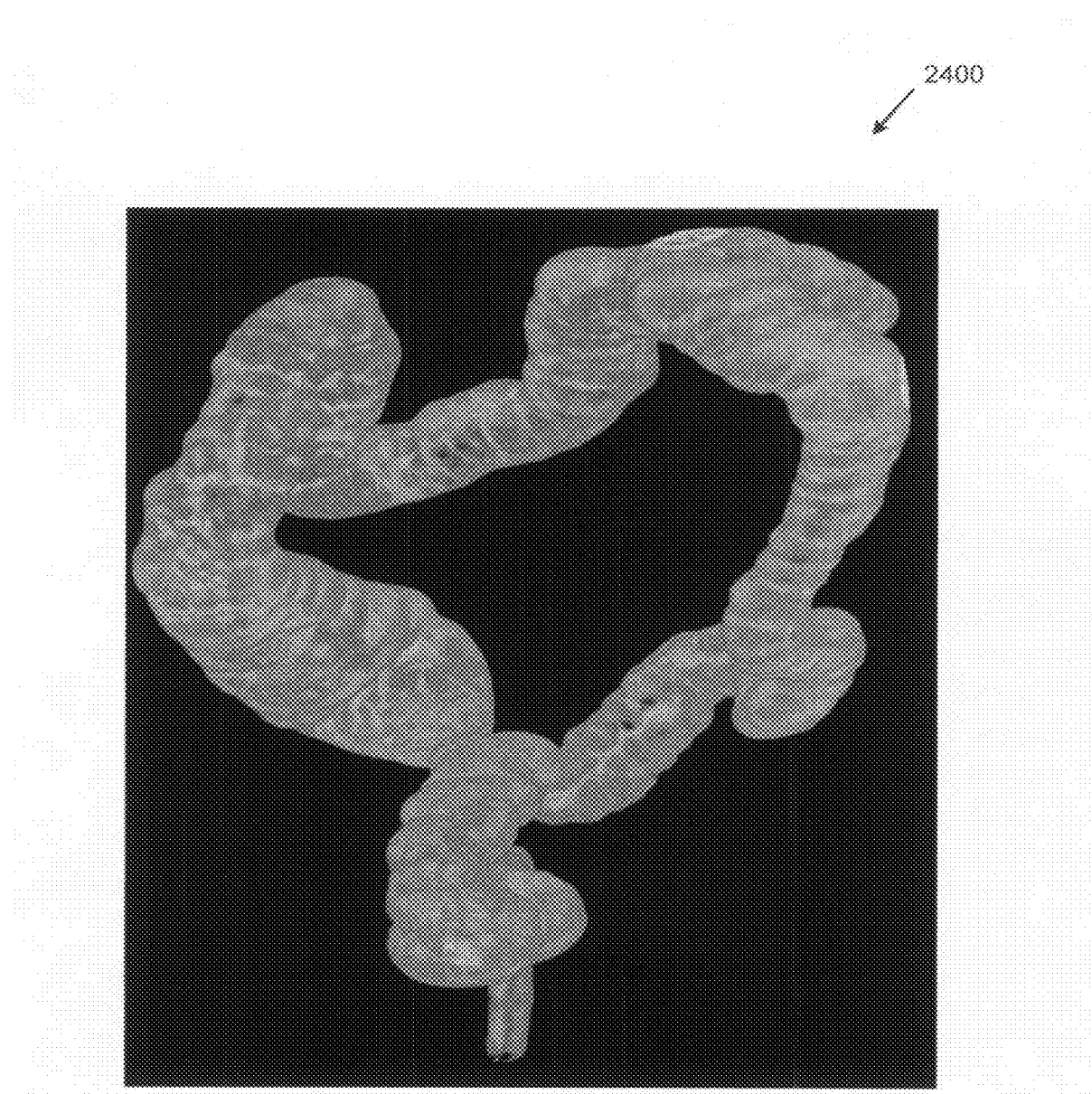
Figure 25:
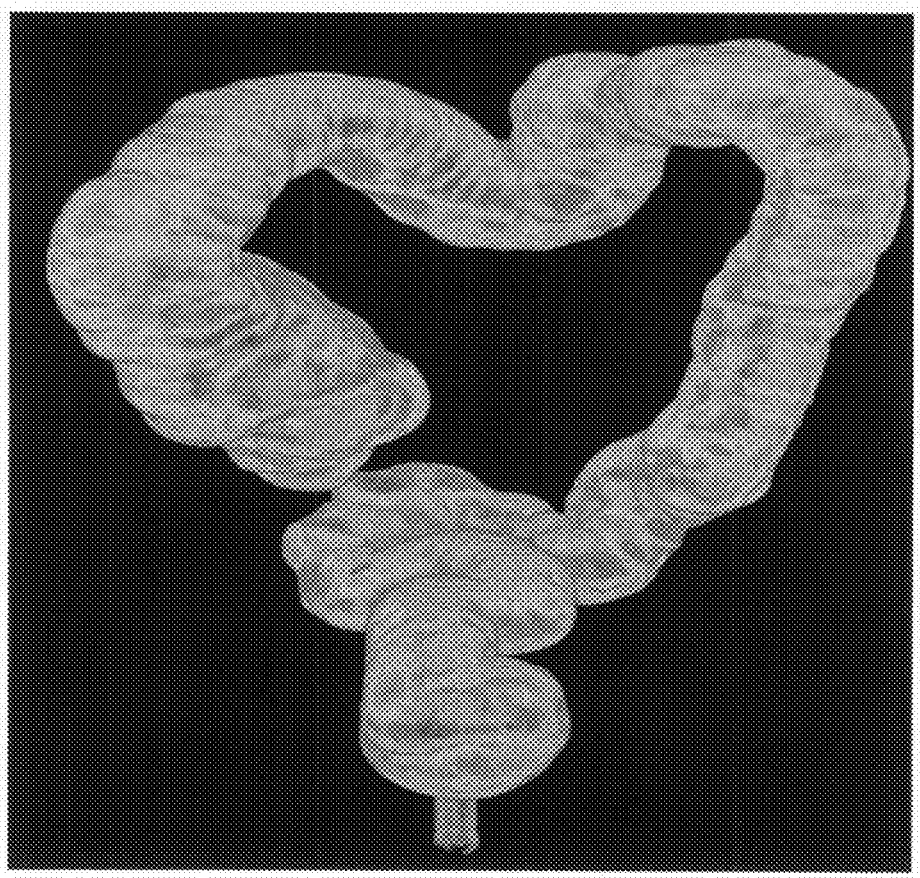
Figure 26:
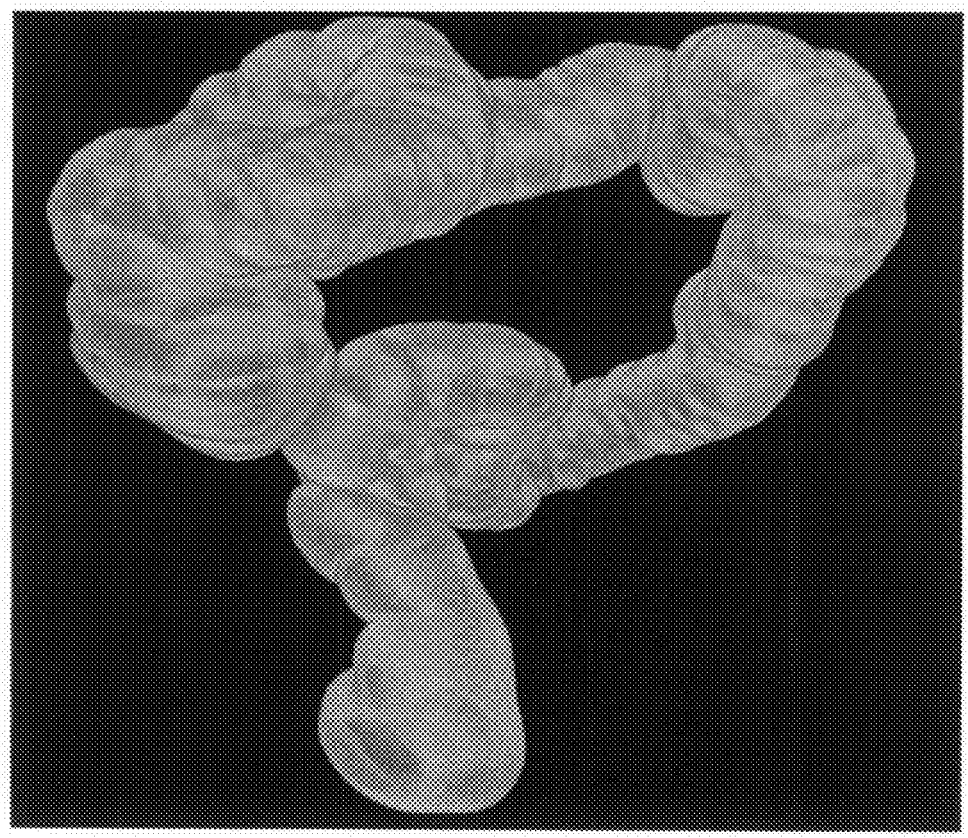

The results of performing level set based segmentation and thickness calculation on the three cases were visualized as shown in FIGS. 24, 25, 26 and 27A-C. FIGS. 24, 25, and 26 show the results of color mapping the thickness on the colon wall. Thicker colon wall areas are indicated by red, while thinner colonic areas are indicated by blue, and average thickness for the particular colon is indicated by the color green.

The average colonic wall thickness was computed to be 4.02±1.80 mm, 4.91±2.04 mm, and 3.66±1.83 mm, respectively. The colonic wall thickness at the polyp location in the colons was 8.0 mm, 10.0 mm, and 4.0 mm, respectively. Regions of interest (e.g., high wall thickness), indicated by the red regions are further visible by lowering the opacity of the blue and green areas, as shown in FIGS. 27A-C.

Figure 28:
Figure 29:
Figure 30:

FIGS. 28, 29, and 30 show the results using the wall thickness to detect potential polyp candidates. The colon inner wall is shown in green; the outer wall is shown in red. Polyp detections are indicated in purple, while false positive detections (e.g., polyp candidates identified but actually not polyps) are shown in blue. The computed results were compared to the optical colonoscopy-proven polyp locations to determine the accuracy of the method. Each polyp was detected by both the wall thickness based and curvature based methods. Table 1 shows the number of false positives that resulted from both of these methods in the analysis of each colon.

TABLE 1

The number of potential polyp candidates calculated based on the curvature and wall thickness methods for the three different colons shown herein.

| Colon | Number of Potential Polyps Based on Curvature | Number of Potential Polyps Based on Wall Thickness | Percentage Potential Polyps Reduction |
|---|---|---|---|
| 1 | 1,163 | 200 | 82.8% |
| 2 | 976 | 499 | 48.9% |
| 3 | 1,274 | 708 | 44.4% |

EXAMPLE 35

Exemplary Further Information

Within the three colons, the majority of the segments have areas that have an average thickness for the respective colon with only isolated areas of increased colon wall thickness. When comparing the computed results to the ground truth (e.g., optical colonoscopy), the polyps in the colons are located in areas that have high colon wall thickness; these results are shown in the zoomed in areas of FIGS. 27A-C. The thick areas of the colon which were not present in the ground truth data as polyps are due to normal variation of the colon wall thickness throughout the colon, due to haustral folds in the colon, due to the different amounts of distention in various areas of the colon, and due to lack of a detectible edge along the outer wall.

The polyps in the three scans were detected by the wall thickness method. Table 1 indicates that the wall thickness method for initial polyp detection results in a reduced number of false positives compared to the curvature based method performed on the same colon. In the example, the techniques involved only initial detection of polyps without feature extraction for each polyp and classification to further eliminate false positives. The majority of the false positives detected by the wall thickness method consisted of enlarged colon wall thickness due to folds and due to difficulty in the lumen segmentation near air-fluid boundaries.

EXAMPLE 36

Exemplary Wall Thickness Techniques

In any of the examples herein, the thickness of the colon wall throughout the colon can be determined. However, such a computation can be time consuming. A binary space partitioning tree can be used to speed up the calculation of the minimum distance between two surfaces at points. Using the partitioning tree, the calculation can be performed in $O(n \log(m))$ time, where n is the number of points on the outer surface, and m is the number of points on the lumen surface.

EXAMPLE 37

Exemplary Level Set Based Thickness Technique

The level set methods described herein for determining the location of the colon outer wall and calculating colonic wall thickness can be used for visually assessing the thickness variations across different regions of the colon and for the initial detection of polyps in the colon. In the experiments, all polyps were detected by the wall thickness method, and the number of false positives generated for each colon was between 44.4% and 82.8% less than the curvature based method. The wall thickness calculation can be used in conjunction with the curvature based method for the detection of polyps to further reduce the final number of false positives detected.

EXAMPLE 38

Exemplary Detection of Colonic Diverticular Disease

The technologies described herein can be used to detect colonic diverticular disease. Estimates state that one third of all individuals have some form of colonic diverticular disease by the age of 50, and approximately two-thirds are affected by the age of 80. Colon wall thickness is a property characteristic of diverticular disease. Accordingly, the techniques described herein can be applied to determine colon wall thickness and detect colonic diverticular disease therefrom.

EXAMPLE 39

Exemplary Techniques for Detection of Colonic Diverticular Disease

Figure 31:
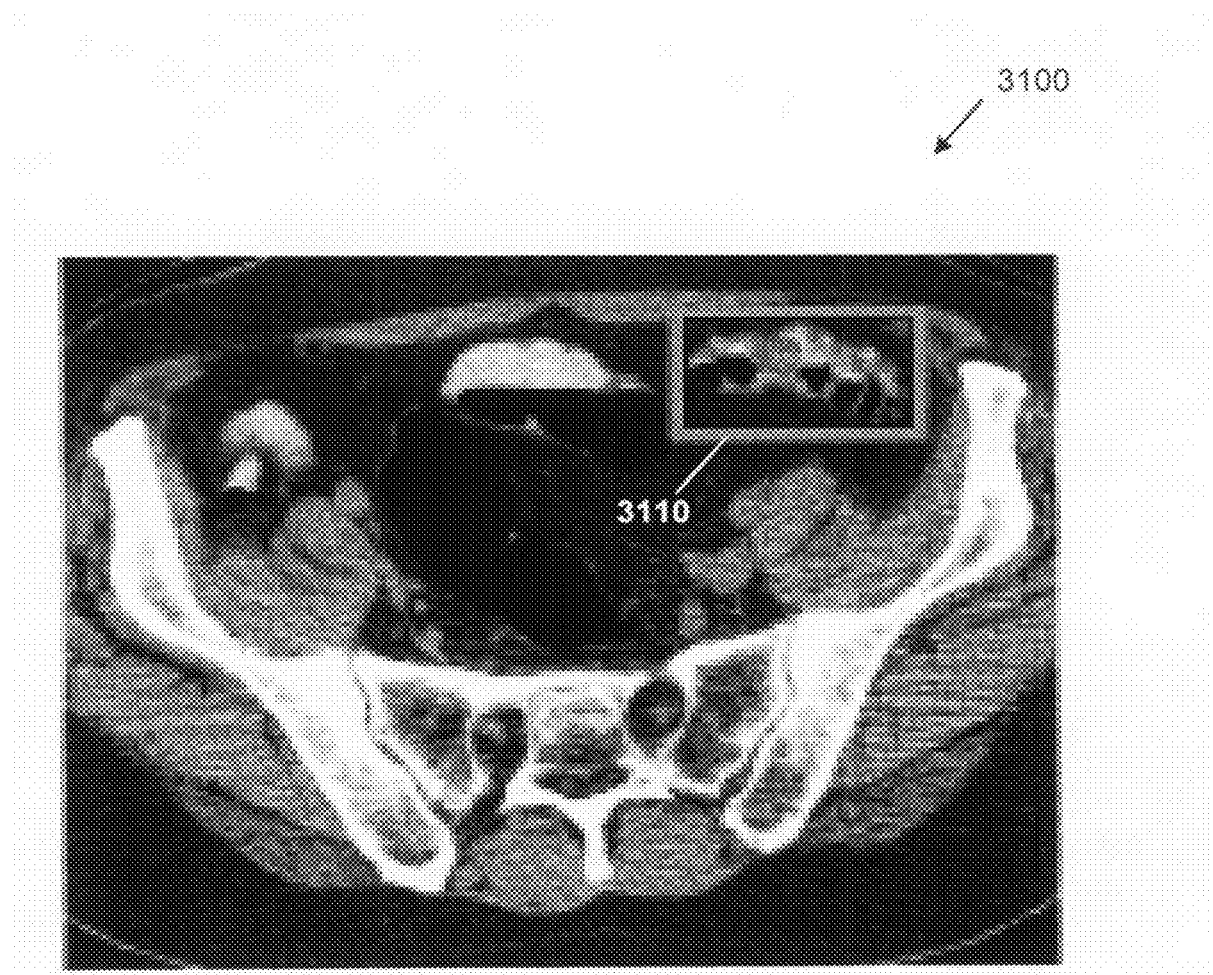
FIG. 31 is a slice of a CTC scan showing colonic wall affected by diverticular disease.
Figure 32:
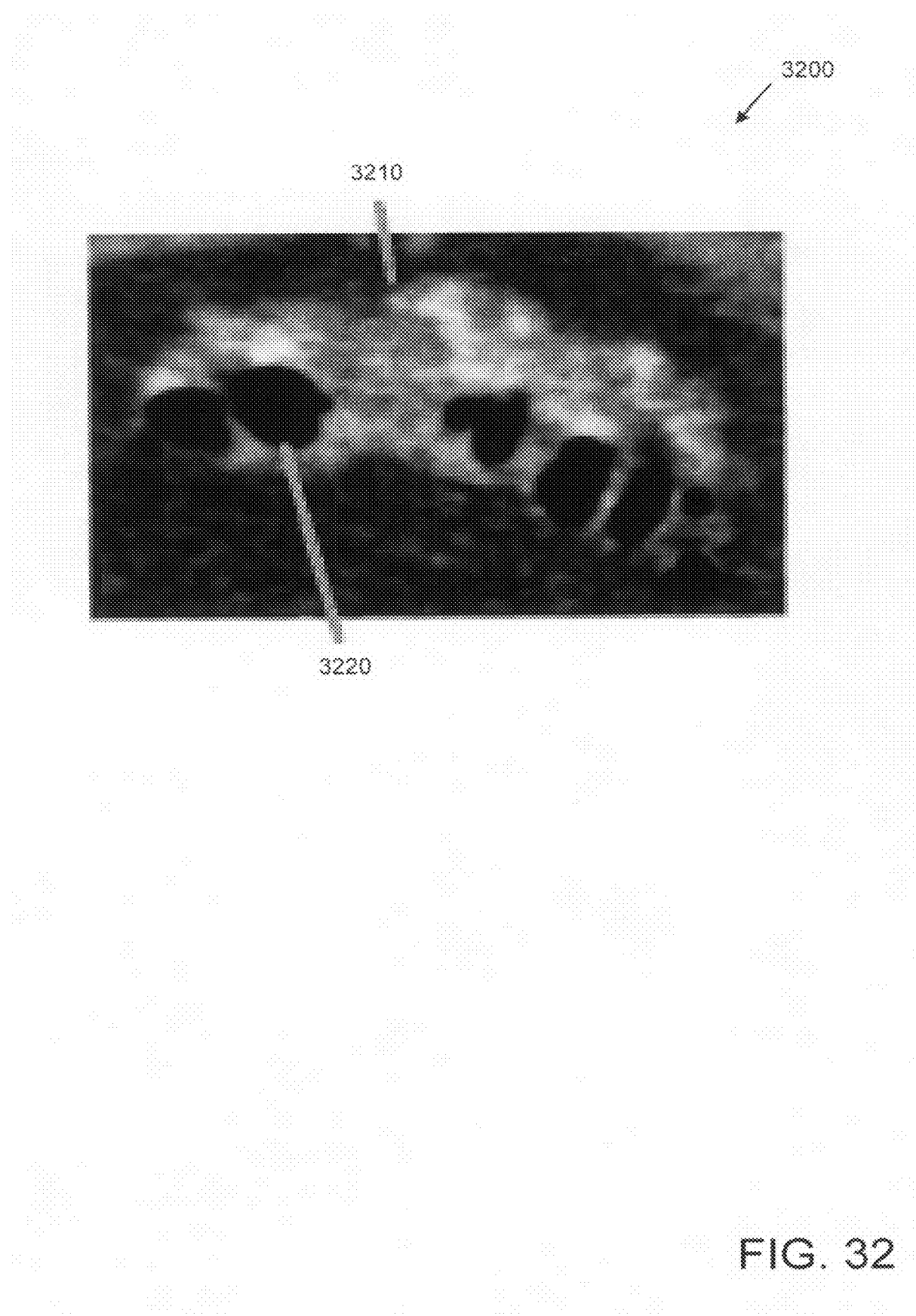
FIG. 32 is an inset of FIG. 31.

The inner and outer walls of the colon can be segmented, and the thickness of the colon wall can be determined. While a normal colonic wall will have a thickness of 1-4 mm, a colonic wall where diverticular disease is present could have a thickness of as much as 10 mm or more. When colonic diverticular disease is present, the thickness of the wall is several millimeters thicker in affected segments (e.g., areas) of the colon than in normal segments of the colon. FIG. 31 is a slice 3100 of a CTC scan showing colonic wall affected by diverticular disease. The portion 3110 of the slice having thickened colonic wall is shown in FIG. 32 as an inset 3200. The outer colon wall (serosal layer) 3210 and the inner colon wall (mucosal layer) 3220 are shown in the inset 3200.

In practice, a variety of techniques can be used to detect diverticular disease. A method for detecting diverticular disease can be to determine wall thickness (e.g., via any of the techniques described herein) and then applying any of a variety of techniques alone or in combination. For example, a threshold thickness can be used. A range of intensities of the colon wall can be used. Detections can be clustered, and various features can be computed per cluster. A support-vector machine can be used to classify whether the features (e.g., for a point, location, or cluster) indicate diverticular disease of the colon.

EXAMPLE 40

Exemplary Segmentation

Figure 33:

FIG. 33 is a slice of a CTC scan showing segmentation of the colon wall as performed via the techniques described herein (e.g., using a value of −500 HU for the lumen-colon inner wall boundary segmentation threshold and determining a subvoxel precise segmentation). The colon inner boundary is shown in green, and the colon outer boundary is shown in red.

EXAMPLE 41

Exemplary Filters for Detection of Diverticular Disease

In any of the examples herein, linear filters can be used to eliminate areas of the colonic outer wall where diverticular disease is not present. Initially, an entire colon or area (e.g., sigmoid colon) thereof can be considered candidate detections. Filters can remove areas that are considered to not have diverticular disease. The filters can be used in conjunction to reduce false positives that remain. For example, a thickness filter and an intensity filter can be applied to reduce false positives.

For example, a filter can be a threshold based on the thickness of the colon wall at the position. A colon wall thickness threshold (e.g., 4 mm or the like) can be used as a threshold for determining the possible presence of diverticular disease. If the wall thickness is less than the threshold, the location or point on the colon can be classified as non-diverticular (e.g., normal). False positives can remain after using the first filter.

Another filter can be the intensity of the colon wall. If the location or point on the outer wall does not contain intensity values between two thresholds experimentally determined as expected values for the colonic wall, the location or point can be classified as being non-diverticular (e.g., diverticular disease is not detected because the colon wall is not involved). For example, a range between −50 and 550 HU or the like can be used.

EXAMPLE 42

Exemplary Clustering for Detection of Diverticular Disease

Because diverticular disease is not a localized disease but will be present throughout whole segments of the colon, detection candidates within a threshold distance can be clustered into a single candidate detection. For example, detections within an n (e.g., 10 or about 10) pixel neighborhood meeting specified criteria can be clustered together and considered a single detection.

For respective clusters (e.g., each cluster), features can be calculated. Such features can include average and standard deviation of the colon wall thickness, and average and standard deviation of the CT intensity values.

The features can then be considered to determine whether the clustered detection indicates colonic diverticular disease.

EXAMPLE 43

Exemplary Classification of Features

In any of the examples herein, a support-vector machine (SVM) can be used for classifying detected features to determine whether a candidate detection indeed indicates colonic diverticular disease. Classification can be performed based on features calculated for detection clusters (e.g., average and standard deviation of the colon wall thickness, and the average and standard deviation of the CT intensity values). Ground truth detection of diverticular disease (e.g., for purposes of configuring the classifier) can be determined by visual inspection of the CT images by a qualified professional. Sensitivity can be calculated on a per-diverticular disease detection basis, and a free-response operating characteristic (FROC) curve can be plotted.

EXAMPLE 44

Exemplary Experimental Results

The diverticular disease detection techniques described herein were performed on ten (10) CT colonoscopy scans each containing volume sizes between 512×512×380 to 512×512×512 images with a spacing of 0.7×0.7×1.00 mm³. Five of the CT scans contained colonic diverticular disease and the other five were from normal patients. Results of the detection of diverticular disease in the sigmoid segment of two different colons can be seen in FIGS. 34 and 35.

Figure 34:
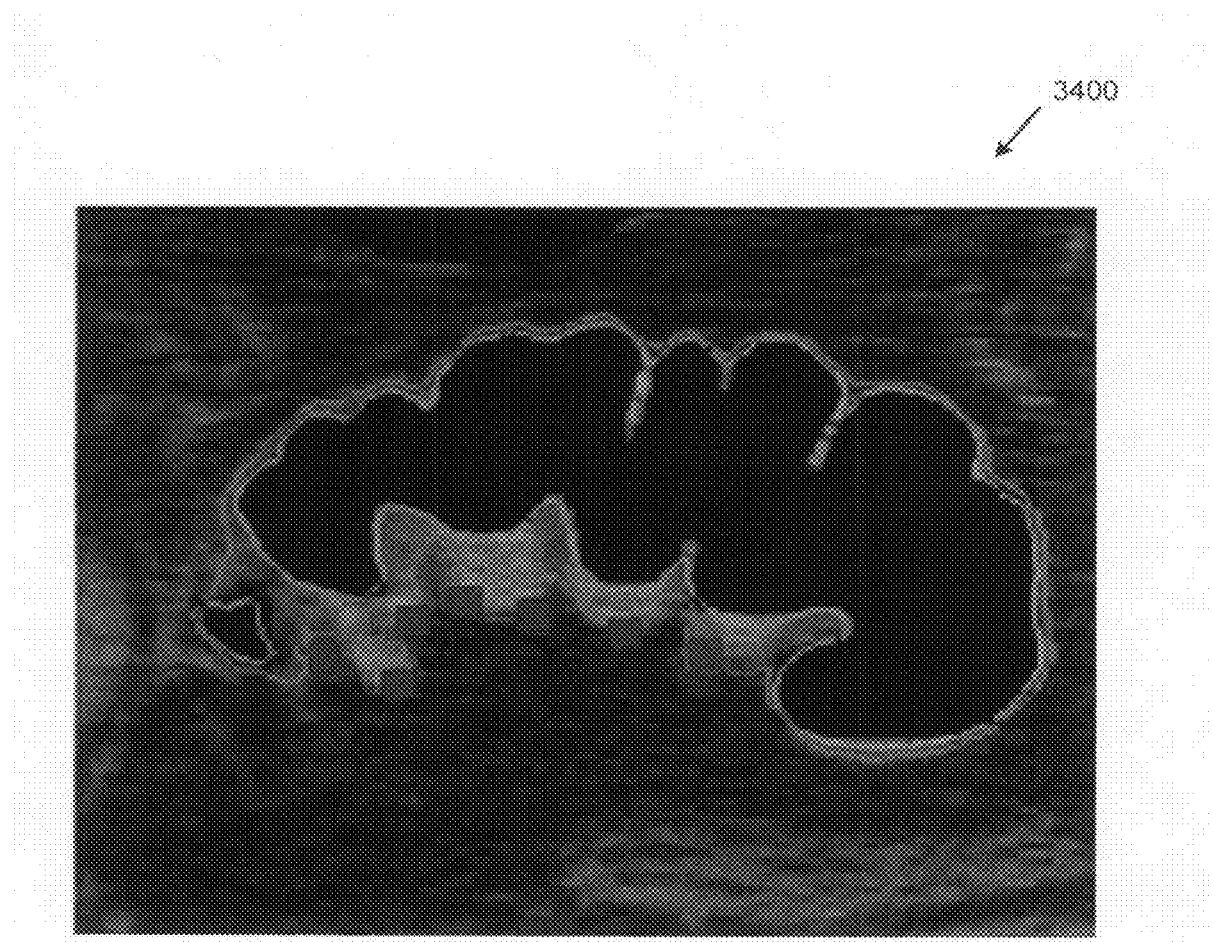
Figure 35:
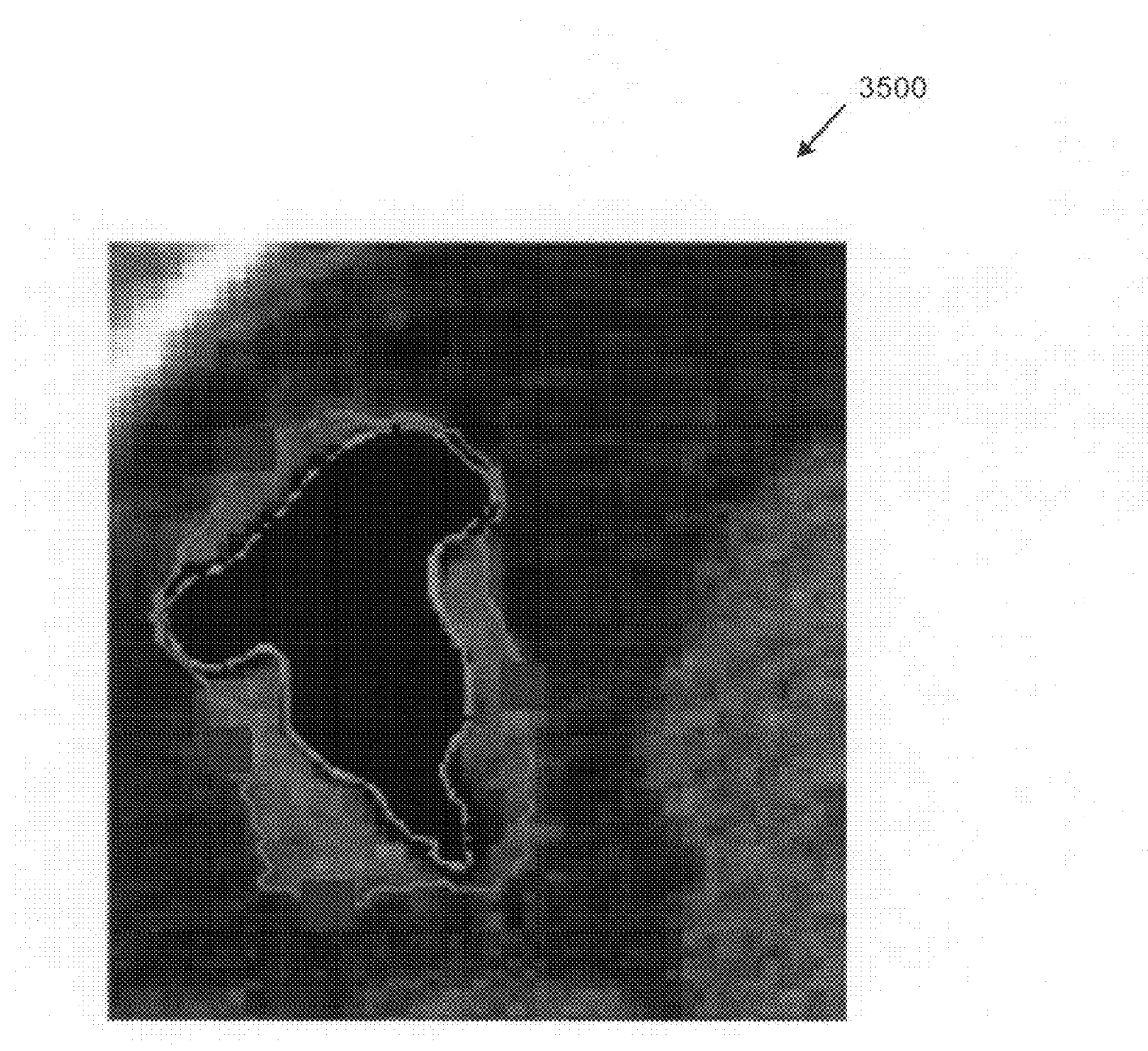

FIGS. 34 and 35 are slices of CTC scans showing the sigmoid portion of two different colons with diverticular disease. The colon inner boundary is shown in green, the colon outer boundary is shown in red, and areas (e.g., clusters) detected as having diverticular disease are shown as blue squares. Although a two-dimensional view is shown, in practice, the locations can be indicated as two-dimensional or three-dimensional locations (e.g., via a coordinate system).

The technique produced 123 detections for the ten data sets, where 87 of them were true positives, and the remaining 36 were false positives. Due to the extent of diverticular disease, multiple true detections may be produced for one disease location. The technique successfully detected all patients having diverticular disease, which corresponds to a sensitivity of 100% at 3.6 false positives per patient.

In order to reduce the false positives further, a support-vector machine (SVM) classifier was run on the four calculated features and produced FROC curves for two cases: one where multiple detections were merged to calculate a sensitivity per patient, and one where multiple detections were not merged to calculate a sensitivity per detection. Merging multiple detections means that any detection for a diverticular disease location was considered as correctly classifying the diverticular disease. In the not merging case, each misclassified detection was counted as a misclassification.

Figure 36:
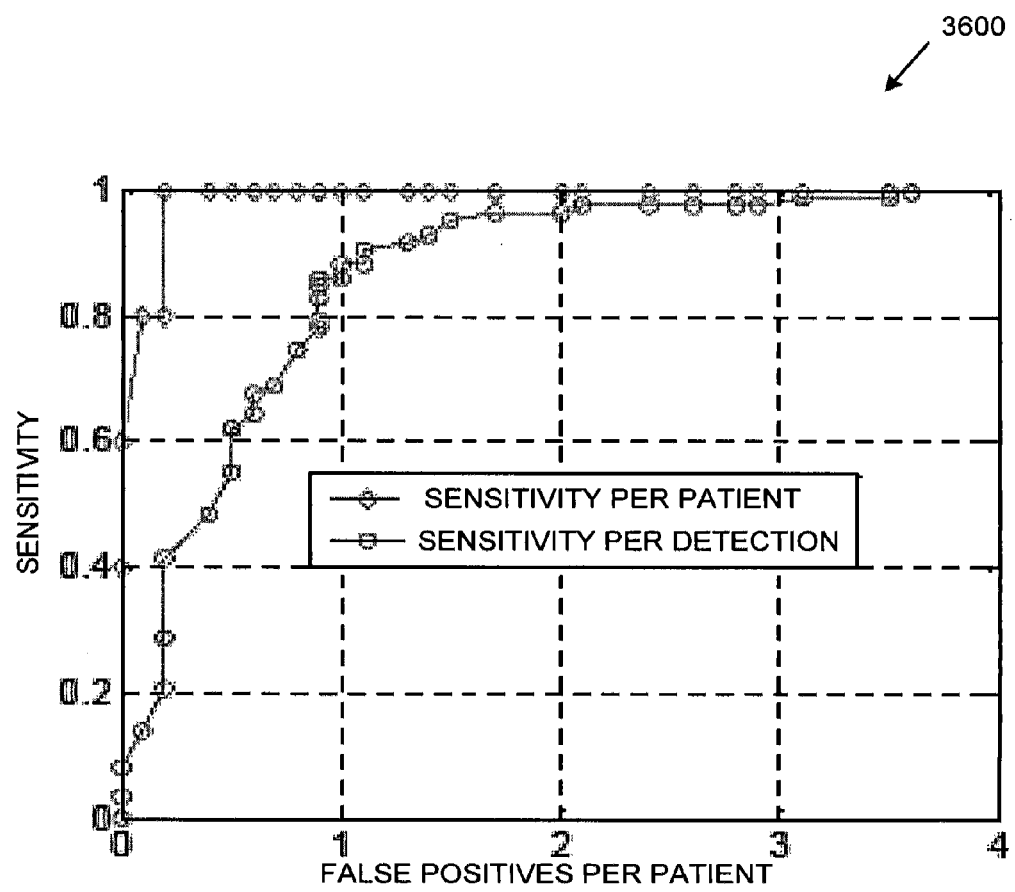
FIG. 36 is a graph of a free-response receiver operating characteristic curve for four features calculated on diverticular detection candidates.

FIG. 36 is a graph of a free-response receive operating characteristic curve for four features calculated on diverticular detection candidates and shows that if the multiple true detections are merged the false positives can be reduced to 0.2 per patient at a sensitivity of 100%. If the multiple true detections are not merged, a sensitivity of 91% can still be obtained for the 87 true detections at 1.1 false positives per patient. The top curve shows sensitivity per patient, and the bottom one shows sensitivity per detection.

EXAMPLE 45

Exemplary Further Information

The results shown in FIGS. 34 and 35 show the accurate segmentation of the colon outer wall. The outer colon wall surfaces generated are subvoxel precise and can be generated fully automatically.

The results of the SVM classification demonstrate the ability of the technique to detect colonic diverticular disease. The FROC curve shows that the false positives of the technique can be 0.2 per patient at a sensitivity of 100%, if the multiple true detections are merged. If the multiple true detections are not merged, the sensitivity for all true detections can be 91% at 1.1 false positives per patient.

Many of the false positives detected by the technique are due to inaccurate segmentation of fluid-filled regions in the colon lumen. The lack of a visible colon wall in normal, well distended portions of the colon also contributes to false positive detections. The other major source of false positives is from the technique mistakenly identifying as colonic wall other organs that abut the colon and have similar CT intensity values as the colon wall, such as the small bowel.

EXAMPLE 46

Exemplary Focus

In any of the examples herein, detection of diverticular disease can be performed for the entire colon or limited to one or more areas therein. For example, detection can be limited to the sigmoid colon because it is the area of the colon that is most often affected by colonic diverticular disease. For example, the digital representation (e.g., image) can be cropped to contain only the sigmoid colon or non-sigmoid areas can be otherwise omitted from analysis.

EXAMPLE 47

Exemplary Anatomical Structures

Although many of the examples herein describe a colon, the technologies can also be applied to any of the other anatomical structures described herein.

The technologies can also be applied to other scenarios involving two or more concentric cylinders (e.g., tree rings, pipes, fruit, or the like).

EXAMPLE 48

Exemplary Anomalies of Interest

Any of the examples herein describing polyp candidates can be applied to anomalies of interest. Exemplary anomalies of interest include noncancerous growths, precancerous growths, and cancerous growths. Such anomalies include polyps, which are growths associated with mucus membranes and epithelial linings. Polyps of interest include colonic, small intestine, nasal, urinary tract, and uterine polyps. Other exemplary anomalies of interest include atherosclerosis and instances of hyperplasia: an abnormal growth of the lining of an organ.

It is important that polyps and other anomalies be detected because they can be premalignant and if detected can be prophylactically removed to avoid development of diseases such as gastrointestinal adenocarcinoma. Thus, early detection enables early treatment (such as removal of the polyp) of possibly life-threatening conditions.

In any of the examples herein, any of the anomalies detected in a digital representation can be analyzed to detect anomalies of interest which correspond to anomalies of interest in the represented real world anatomical structure. Various software filtering mechanisms as described herein can be used on an initial list of detected anomalies of interest (e.g., polyp candidates) to provide a resulting list of anomalies of interest (e.g., confirmed candidates).

EXAMPLE 49

Exemplary Improvements Gained by Using Exemplary Embodiments Herein

The embodiments disclosed herein present a segmentation technique that can be implemented fully-automatically, and which does not require user interaction.

EXAMPLE 50

Exemplary Acquisition of Digital Representations

A variety of technologies can be used to acquire three-dimensional digital representations for use with the technologies described herein. Acquisition of a representation of an anatomical structure is typically done by performing a scan of the soft tissues of the patient. For example, a CT scan can be performed according to any number of standard protocols. CT scans can be used to generate thin-section CT data (for example, helical scan CT data). The representation can be analyzed immediately after the scan, or the representation can be stored for later retrieval and analysis. Exemplary technologies for acquiring scans are described in Pickhardt et al., "Computed Tomographic Virtual Colonoscopy to Screen for Colorectal Neoplasia in Asymptomatic Adults," *New Engl. J. Med.*, 349:2191 (2003), Vining et al., "Virtual Colonoscopy," *Radiology* 193(P):446 (1994), Vining et al., "Virtual Bronchoscopy," *Radiology* 193(P):261 (1994), and Vining et al., "Virtual bronchoscopy. Relationships of virtual reality endobronchial simulations to actual bronchoscopic findings" *Chest* 109(2): 549-553 (February 1996).

Any number of hardware implementations can be used to acquire a representation of an anatomical structure. For example, the GE HiSpeed Advantage scanner of GE Medical Systems, Milwaukee, Wis. can be used.

Additional exemplary segmentation technologies are described in U.S. Pat. No. 6,556,696 to Summers et al., filed Feb. 5, 2002, entitled, "METHOD FOR SEGMENTING MEDICAL IMAGES AND DETECTING SURFACE ANOMALIES IN ANATOMICAL STRUCTURES," which is hereby incorporated herein by reference.

EXAMPLE 51

References

The following references are hereby incorporated by reference herein:

[1] A. Jemal, R. C. Tiwari, T. Murray, A. Ghafoor, A. Samuels, E. Ward, E. J. Feuer, M. J. Thun. Cancer statistics, 2004. *CA Cancer J Clin,* 54:8-29, 2004.

[2] T. M. Gluecker, C. D. Johnson, W. S. Harmsen, K. P. Offord, A. M. Harris, L. A. Wilson, D. A. Ahlquist. Colorectal cancer screening with CT colonography, colonoscopy, and double-contrast barium enema examination: prospective assessment of patient perceptions and preferences. *Radiology,* 227:378-84, 2003.

[3] R. M. Summers, J. Yao, P. J. Pickhardt, M. Franaszek, I. Bitter, D. Brickman, V. Krishna, J. R. Choi. Computed Tomographic Colonoscopy Computer-Aided Polyp Detection in a Screening Population. *Gastroenterology,* 129: 1832-1844, 2005.

[4] J. A. Sethian. *Level Set Methods and Fast Marching Methods: Evolving Interfaces in Computational Geometry, Fluid Mechanics, Computer Vision, and Materials Science.* Cambridge University Press, 1999.

[5] R. Kimmel, V. Caselles, G. Saprio. Geodesic active contours. *International Journal on Computer Vision,* 22(1):61-97, 1997.

[6] R. M. Summers, A. K. Jerebko, M. Franaszek, J. D. Malley, C. D. Johnson. Colonic Polyps: complementary role of computer-aided detection in CT colonography. *Radiology* 225:391-399, 2002.

[7] M. Franaszek, R. M. Summers, P. J. Pickhardt, J. R. Choi. Hybrid Segmentation of Colon Filled with Air and Opacified Fluid for CT colonography. *IEEE Tras. Med.* 1 mg. 25: 358-368, 2006.

[8] Z. Wang, A. Liang, L. Li, X. Li, B. Li, J. Anderson, D. Harrington. Reduction of false positives by internal features for polyp detection in CT-based virtual colonoscopy. *Medical Physics,* 32: 3602-3615, 2005.

[9] Z. Zeng, L. H. Staib, R. T. Schultz, and J. S. Duncan. Segmentation and Measurement of the Cortex from 3-D MR Images Using Coupled—Surfaces Propagation. *IEEE Trans. Med.* 1 mg, 18:927-937, 1999.

EXAMPLE 52

Exemplary Computer System for Conducting Analysis

Figure 37:
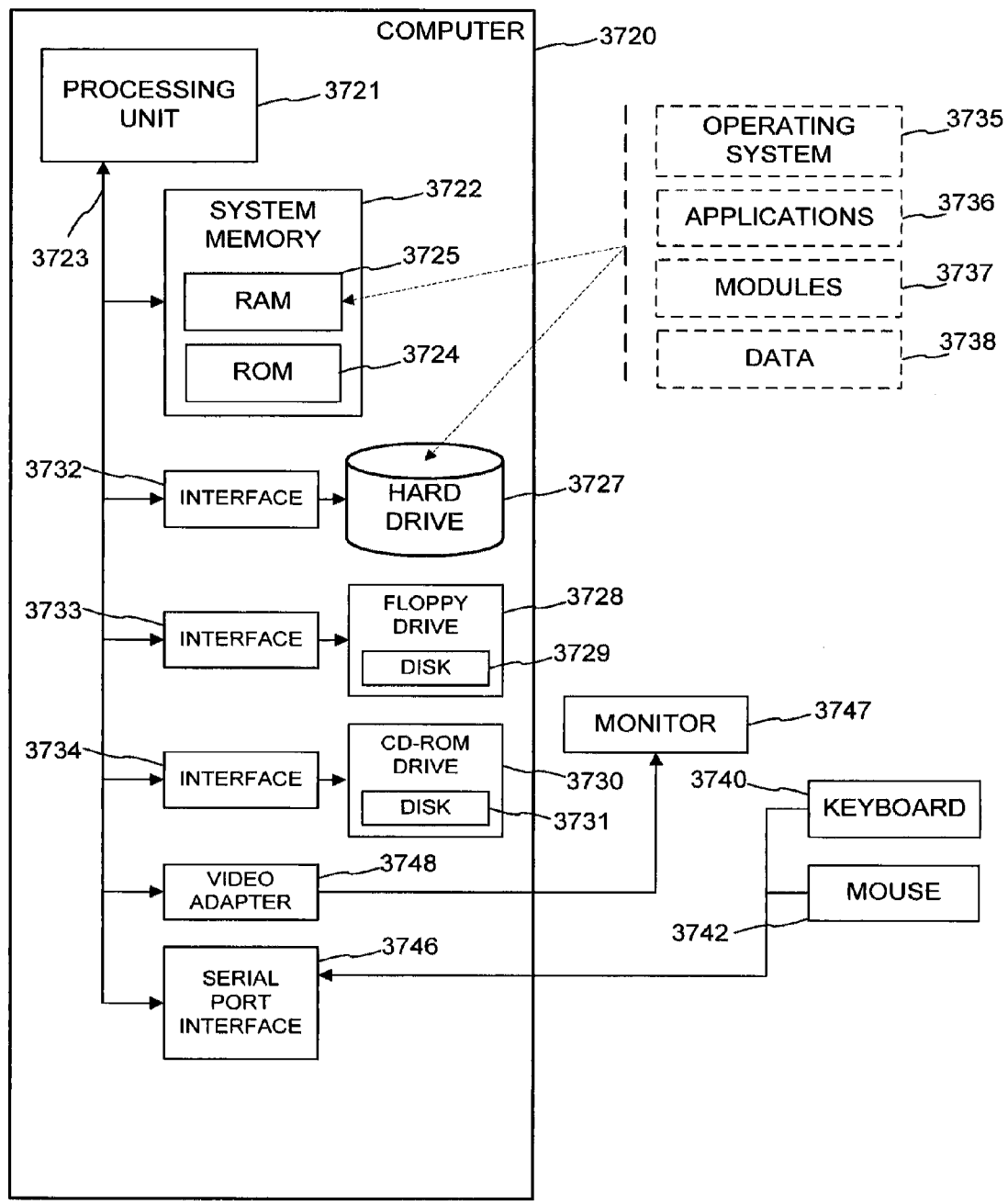
FIG. 37 is a block diagram of an exemplary computer system for implementing the described technologies.

FIG. 37 and the following discussion provide a brief, general description of a suitable computing environment for the software (for example, computer programs) described above. The methods described above can be implemented in computer-executable instructions (for example, organized in program modules). The program modules can include the routines, programs, objects, components, and data structures that perform the tasks and implement the data types for implementing the technologies described above.

While FIG. 37 shows a typical configuration of a desktop computer, the technologies may be implemented in other computer system configurations, including multiprocessor systems, microprocessor-based or programmable consumer electronics, minicomputers, mainframe computers, and the like. The technologies may also be used in distributed computing environments where tasks are performed in parallel by processing devices to enhance performance. For example, tasks related to measuring characteristics of anomalies of interest can be performed simultaneously on multiple computers, multiple processors in a single computer, or both. In a distributed computing environment, program modules may be located in both local and remote memory storage devices.

The computer system shown in FIG. 37 is suitable for implementing the technologies described herein and includes a computer 3720, with a processing unit 3721, a system memory 3722, and a system bus 3723 that interconnects various system components, including the system memory to the processing unit 3721. The system bus may comprise any of several types of bus structures including a memory bus or memory controller, a peripheral bus, and a local bus using a bus architecture. The system memory includes read only memory (ROM) 3724 and random access memory (RAM) 3725. A nonvolatile system (for example, BIOS) can be stored in ROM 3724 and contains the basic routines for transferring information between elements within the personal computer 3720, such as during start-up. The personal computer 3720 can further include a hard disk drive 3727, a magnetic disk drive 3728, for example, to read from or write to a removable disk 3729, and an optical disk drive 3730, for example, for reading a CD-ROM disk 3731 or to read from or write to other optical media. The hard disk drive 3727, magnetic disk drive 3728, and optical disk 3730 are connected to the system bus 3723 by a hard disk drive interface 3732, a magnetic disk drive interface 3733, and an optical drive interface 3734, respectively. The drives and their associated computer-readable media provide nonvolatile storage of data, data structures, computer-executable instructions (including program code such as dynamic link libraries and executable files), and the like for the personal computer 3720. Although the description of computer-readable media above refers to a hard disk, a removable magnetic disk, and a CD, it can also include other types of media that are readable by a computer, such as magnetic cassettes, flash memory cards, DVDs, and the like.

A number of program modules may be stored in the drives and RAM 3725, including an operating system 3735, one or more application programs 3736, other program modules 3737, and program data 3738. A user may enter commands and information into the personal computer 3720 through a keyboard 3740 and pointing device, such as a mouse 3742. Other input devices (not shown) may include a microphone, joystick, game pad, satellite dish, scanner, or the like. These and other input devices are often connected to the processing unit 3721 through a serial port interface 3746 that is coupled to the system bus, but may be connected by other interfaces, such as a parallel port, game port, or a universal serial bus (USB). A monitor 3747 or other type of display device is also connected to the system bus 3723 via an interface, such as a display controller or video adapter 3748. In addition to the monitor, personal computers typically include other peripheral output devices (not shown), such as speakers and printers.

The above computer system is provided merely as an example. The technologies can be implemented in a wide variety of other configurations. Further, a wide variety of approaches for collecting and analyzing data related to processing anomalies of interest is possible. For example, the data can be collected, characteristics determined and measured, anomalies classified and reclassified, and the results presented on different computer systems as appropriate. In addition, various software aspects can be implemented in hardware, and vice versa.

EXAMPLE 53

Exemplary Methods

Any of the methods described herein can be performed by software executed by software in an automated system (for example, a computer system). Fully-automatic (for example, without human intervention) or semi-automatic operation (for example, computer processing assisted by human intervention) can be supported. User intervention may be desired in some cases, such as to adjust parameters or consider results.

Such software can be stored on one or more computer-readable media (e.g., storage media or other tangible media) comprising computer-executable instructions for performing the described actions (e.g., causing a computer to perform actions of the methods shown).

ALTERNATIVES

Having illustrated and described the principles of the invention in exemplary embodiments, it is noted that the described examples are illustrative embodiments and can be modified in arrangement and detail without departing from such principles. Technologies from any of the examples can be incorporated into one or more of any of the other examples.

In view of the many possible embodiments to which the principles of the invention may be applied, it should be understood that the illustrative embodiments are intended to teach these principles and are not intended to be a limitation on the scope of the invention. We therefore claim as our invention all that comes within the scope and spirit of the following claims and their equivalents.

We claim:
1. A computer-implemented method comprising:
receiving a digital representation for a colon, wherein the digital representation represents at least a portion of a colon wall for the colon;
identifying an outer boundary for the colon wall via a level set technique; and
outputting an indication of the outer boundary of the colon wall;
wherein the level set technique comprises:
generating a speed image; and
evolving an isosurface based at least on the speed image;
wherein identifying the outer boundary for the colon wall via the level set technique comprises:
using a lumen segmentation of the digital representation as an initial level set boundary.

2. One or more non-transitory computer-readable media comprising computer-executable instructions causing a computer to perform a method comprising:
- receiving a digital representation for a colon, wherein the digital representation represents at least a portion of a colon wall for the colon;
- identifying an outer boundary for the colon wall via a level set technique; and
- outputting an indication of the outer boundary of the colon wall;
- wherein the level set technique comprises:
- generating a speed image; and
- evolving an isosurface based at least on the speed image;
- wherein identifying the outer boundary for the colon wall via the level set technique comprises:
- using a lumen segmentation of the digital representation as an initial level set boundary.

3. The computer-implemented method of claim 1 wherein the indication of the outer boundary of the colon wall is of subvoxel accuracy.

4. The computer-implemented method of claim 1 wherein the level set technique comprises three-dimensional geodesic active contour level set segmentation.

5. The computer-implemented method of claim 1 further comprising:
- identifying an inner boundary of the colon wall; and
- via the inner boundary of the colon wall and the outer boundary of the colon wall, calculating a thickness of the colon wall.

6. The computer-implemented method of claim 5 wherein:
- the outer boundary of the colon wall is represented as a surface;
- the inner boundary of the colon wall is represented as a surface; and
- calculating thickness comprises determining distance between the surfaces.

7. The computer-implemented method of claim 5 further comprising:
- submitting a set of characteristics for a polyp candidate to a polyp candidate classifier configured to determine whether the polyp candidate is a true positive;
- wherein the set of characteristics comprises the thickness of the colon wall.

8. The computer-implemented method of claim 1 further comprising:
- segmenting the colon wall.

9. The computer-implemented method of claim 8 further comprising:
- determining a thickness of the colon wall.

10. The computer-implemented method of claim 8 further comprising:
- detecting colonic diverticular disease via the thickness of the colon wall.

11. The computer-implemented method of claim 8 further comprising:
- detecting colon spasm via the thickness of the colon wall.

12. The computer-implemented method of claim 8 further comprising:
- detecting colon cancer via the thickness of the colon wall.

13. The computer-implemented method of claim 8 further comprising:
- detecting presence of a polyp via the thickness of the colon wall.

14. The computer-implemented method of claim 1 wherein:
- identifying the outer boundary for the colon wall comprises identifying at least a location of the outer boundary of the colon wall; and
- the indication of the outer boundary of the colon wall indicates at least the location of the outer boundary of the colon wall.

15. A computer-implemented method comprising:
- receiving a digital representation for a colon, wherein the digital representation represents at least a portion of a colon wall for the colon;
- identifying an outer boundary for the colon wall via a level set technique; and
- outputting an indication of the outer boundary of the colon wall;
- wherein the level set technique comprises:
- generating a speed image; and
- evolving an isosurface based at least on the speed image;
- wherein generating the speed image comprises:
- calculating a directional derivative of the digital representation in a direction perpendicular to a colon wall inner boundary represented in a colon wall inner boundary segmentation.

16. The computer-implemented method of claim 15 further comprising:
- suppressing local non-maximum gradients along a level set expansion direction via a sigmoid filter.

17. The computer-implemented method of claim 15 further comprising:
- performing a lumen segmentation for the digital representation; and
- using a lumen boundary in the lumen segmentation as the colon wall inner boundary segmentation.

18. The computer-implemented method of claim 17 wherein the lumen segmentation comprises:
- generating a threshold region growing segmentation; and
- segmenting via a threshold level set technique, wherein the threshold level set technique uses the threshold region growing segmentation as an initial level set boundary.

19. The computer-implemented method of claim 1 wherein:
- the speed image is determined via the digital representation for the colon.

20. The computer-implemented method of claim 1 further comprising:
- segmenting an entire colon wall of the colon.

21. A computer-implemented method comprising:
- receiving a three-dimensional digital representation for a colon, wherein the digital representation comprises a computed tomography image representing at least a portion of a colon wall for the colon;
- from the digital representation for the colon, generating a lumen segmentation indicating a boundary of an inner wall of the colon;
- producing lumen segmentation level sets from the lumen segmentation;
- from the lumen segmentation and the computed tomography image, generating a speed image via a three-dimensional derivative of the computed tomography image in a direction perpendicular to lumen segmentation level sets, wherein local non-maximum gradients along level set expansion direction are suppressed, and generating the speed image comprises applying a sigmoid filter emphasizing high directional derivatives and inverting the speed image;
- generating a level set image via a level set segmentation of an outer wall of the colon via three-dimensional geodesic active contour level set segmentation with the speed image, wherein the lumen segmentation level sets are used as an initial level set boundary, an advection term attracts level set evolution to high gradient values, and a curvature term prevents evolution of the boundary from exceeding a maximum curvature;

determining a boundary of the outer wall of the colon via an isocontour in the level set image; and outputting an indication of the boundary of the outer wall of the colon.

22. A computer-implemented method comprising:
receiving a digital representation for a colon, wherein the digital representation represents at least a portion of a wall for the colon;
determining wall thickness for the wall, wherein determining wall thickness for the wall comprises applying a level set technique to the digital representation; and
detecting presence of colonic diverticular disease via determined wall thickness for the wall.

23. The method of claim 22 wherein determining wall thickness for the wall comprises applying a binary space partitioning tree.

24. The method of claim 22 wherein detecting presence of colonic diverticular disease comprises:
clustering candidate detections within a threshold distance.

25. The method of claim 22 wherein detecting presence of colonic diverticular disease comprises:
responsive to determining that a location on the colon is under a threshold thickness, classifying the location as not having diverticular disease.

26. The method of claim 22 wherein detecting presence of colonic diverticular disease comprises:
responsive to determining that CT intensity of a location on an outer wall of the colon is outside of a normal range for colon wall, classifying the location as not being a detection of diverticular disease.

27. The method of claim 22 wherein detecting presence of colonic diverticular disease comprises:
computing an average and standard deviation of colon wall thickness for a cluster of locations.

28. The method of claim 22 wherein detecting presence of colonic diverticular disease comprises:
computing an average and standard deviation of intensity values for a cluster of locations.

29. The method of claim 22 wherein detecting presence of colonic diverticular disease comprises:
providing a plurality of features for a cluster of locations to a support-vector machine classifier configured to indicate whether the cluster of locations are indicative of colonic diverticular disease.

30. One or more non-transitory computer-readable media comprising computer-executable instructions causing a computer to perform a method comprising:
receiving a digital representation for a colon, wherein the digital representation represents at least a portion of a wall for the colon;
determining wall thickness for the wall, wherein determining wall thickness for the wall comprises applying a level set technique to the digital representation; and
detecting presence of colonic diverticular disease via determined wall thickness for the wall.

31. A computer-implemented method comprising:
receiving a digital representation for a colon, wherein the digital representation represents at least a portion of a colon wall for the colon;
identifying an outer boundary for the colon wall via a level set technique; and
outputting an indication of the outer boundary of the colon wall;
wherein the level set technique comprises:
generating a speed image; and
evolving an isosurface based at least on the speed image;
wherein the indication of the outer boundary of the colon wall is of subvoxel accuracy.

32. One or more non-transitory computer-readable media comprising computer-executable instructions causing a computer to perform a method comprising:
receiving a digital representation for a colon, wherein the digital representation represents at least a portion of a colon wall for the colon;
identifying an outer boundary for the colon wall via a level set technique; and
outputting an indication of the outer boundary of the colon wall;
wherein the level set technique comprises:
generating a speed image; and
evolving an isosurface based at least on the speed image;
wherein the indication of the outer boundary of the colon wall is of subvoxel accuracy.

* * * * *